United States Patent
Yamamoto et al.

(10) Patent No.: US 6,914,155 B2
(45) Date of Patent: Jul. 5, 2005

(54) HIGH POLYMER GEL AND ACTIVATION METHOD FOR COMPOUNDS CONTAINING ACTIVE HYDROGEN

(75) Inventors: Hiroshi Yamamoto, Suita (JP); Yoshiaki Hirano, Suita (JP)

(73) Assignee: Nippon Shokubai Co., Ltd., Osaka (JP)

( * ) Notice: Subject to any disclaimer, the term of this patent is extended or adjusted under 35 U.S.C. 154(b) by 71 days.

(21) Appl. No.: 09/916,700

(22) Filed: Jul. 27, 2001

(65) Prior Publication Data

US 2002/0028872 A1 Mar. 7, 2002

Related U.S. Application Data

(62) Division of application No. 09/297,953, filed as application No. PCT/JP98/04021 on Sep. 7, 1998, now abandoned.

(30) Foreign Application Priority Data

Sep. 8, 1997 (JP) .............................................. 9-243135

(51) Int. Cl.[7] .............................................. C07C 67/26
(52) U.S. Cl. ...................................... 560/209; 560/210
(58) Field of Search ................................. 560/209, 210

(56) References Cited

U.S. PATENT DOCUMENTS

| 3,340,295 A | * | 9/1967 | Wheeler et al. ............. 560/209 |
| 3,716,481 A | | 2/1973 | Battaerd et al. ............... 210/32 |
| 3,804,884 A | * | 4/1974 | Clayton et al. .............. 560/209 |
| 3,891,576 A | | 6/1975 | Battaerd et al. ......... 260/2.1 R |
| 3,941,724 A | | 3/1976 | Bolto ...................... 260/2.1 R |
| 4,069,242 A | * | 1/1978 | Gurgiolo ...................... 560/93 |
| 4,970,333 A | * | 11/1990 | Rabon et al. ................ 560/209 |
| 5,354,896 A | * | 10/1994 | Pike et al. ................... 560/209 |

FOREIGN PATENT DOCUMENTS

| EP | 0 841 350 A1 | 5/1998 |
| EP | 1 022 058 A1 | 7/2000 |
| JP | 49-31631 | 8/1974 |
| JP | 54-148705 | 11/1979 |
| JP | 58-117208 | 7/1983 |
| JP | 6-70785 | 3/1994 |
| JP | 6-320009 | 11/1994 |
| JP | 9-290163 | 11/1997 |

* cited by examiner

Primary Examiner—Bernard Lipman
(74) Attorney, Agent, or Firm—David C. Conlin; John B. Alexander; Edwards & Angell, LLP

(57) ABSTRACT

Active hydrogen in an active-hydrogen-containing compound is activated by using a polymer gel having a three-dimensional network structure holding a solvent inside thereof and active sites inside the three-dimensional network structure and surfaces thereof. The ratio of swell of the polymer gel is preferably set to not less than 2, and it is preferable for the polymer gel to have a basic functional group derived from at least one compound selected from the group consisting of tertiary amine compounds, quaternary ammonium salts, cyclic amine compounds and sulfides. The activation of active hydrogen in the active-hydrogen-containing compound is preferably carried out under the condition that the amount of basic active sites of the polymer gel per unit volume in the active system accompanying the activation of active hydrogen is set to not less than 0.43 mmol/cc.

16 Claims, No Drawings

HIGH POLYMER GEL AND ACTIVATION METHOD FOR COMPOUNDS CONTAINING ACTIVE HYDROGEN

This application is a divisional of application(s) application Ser. No. 09/297,953. The nonprovisional application designated above, namely application Ser. No. 09/297,953, filed Jul. 21, 1999, now abandoned, claims the benefit of Application(s) No(s).: PCT/JP98/04021 filing date Sep. 7, 1998.

FIELD OF THE INVENTION

The present invention relates to a polymer gel and an activation method for active-hydrogen-containing compounds using such a polymer gel.

BACKGROUND OF THE INVENTION

Conventionally, a large number of studies have been made on reaction processes using catalysts in, for example, hydration reactions of olefins and polymerization reactions, etc. Generally, catalysts are classified into homogeneous catalysts in which the catalyst phase is the same as the reaction phase, such as an acid catalyst, etc. in a solution, and heterogeneous catalysts in which the catalyst phase is different from the reaction phase, such as a solid catalyst added to a reaction system of a gas phase or a liquid phase.

In the homogeneous catalyst, the active component is in the same phase as the homogeneous reaction system, and, for example, the reaction progresses with the active component being uniformly dispersed in the solution. Consequently, the reaction rate is fast and the reaction substrate has a high conversion. Therefore, its catalyst design is easily made. However, disadvantages of the homogeneous catalyst are that difficult operations are required in separating the catalyst and that waste liquid is inevitably produced, thereby necessitating waste-liquid treatments.

In contrast, in the heterogeneous catalyst, the separation operation is comparatively easy, and no waste liquid is produced, which is advantageous in carrying out processes after the reaction. However, in the heterogeneous catalyst, such as, for example, an ion exchange resin, the reaction progresses with a functional group fixed onto the surface of a carrier or a base material serving as an active site; therefore, the reaction takes place on the catalyst surface. For this reason, in the case when a heterogeneous catalyst is used as a catalyst, the reaction rate is slow, and the reaction substrate has a low conversion. Therefore, the application of the heterogeneous catalyst as a catalyst makes the catalyst design difficult. Moreover, in order to improve the reaction rate, the above-mentioned conventional solid catalyst requires severe settings of reaction conditions, such as high temperatures and high pressure during the reaction, and it also have a problem of greater degradation upon reaction.

In particular, ion exchange resins, such as basic ion exchange resins which have conventionally been known as basic resins, are inferior in heat resistance; therefore, they require limited conditions upon application, and tend to deteriorate due to heat even under their heat resistant temperature (applicable temperature), with the result that their exchange groups are separated and their activity is lowered.

In other words, the above-mentioned conventional catalysts are inferior in the balance between the operability in separation operation, etc. and the catalyst activity such as reaction rates and conversion of reaction substrate, and fail to simultaneously satisfy both of them. Therefore, there are ever-increasing demands for a catalyst which provides an easy separation operation from the reaction system and can activate the active-hydrogen-containing compound efficiently, and for an activation method for the active-hydrogen-containing compound which provides an easy separation operation from the reaction system and can activate the active-hydrogen-containing compound efficiently.

DISCLOSURE OF THE INVENTION

The present invention has been devised to solve the above-mentioned problems, and its objective is to provide an activation method for active-hydrogen-containing compounds and an activation catalyst, which can provide an easy separation operation for the catalyst and can efficiently activate active-hydrogen-containing compounds.

In order to achieve the above-mentioned objective, the inventors, etc. of the present invention have made extensive research efforts, and found that a polymer gel, which has a three-dimensional network structure holding solvent inside thereof, and also has active sites inside the three-dimensional network structure and/or on the surface thereof, exhibits a superior catalyst activation, can activate active hydrogen contained in an active-hydrogen containing compound efficiently, and provide an easy separation operation; thus, the present invention has been completed.

In other words, in order to solve the above-mentioned problems, the activation catalyst for active-hydrogen-containing compounds of the present invention is characterized in that active hydrogen in an active-hydrogen-containing compound is activated by using a polymer gel.

Moreover, in order to solve the above-mentioned problems, the activation catalyst for active-hydrogen-containing compounds of the present invention is characterized in that it has a three-dimensional network structure holding solvent inside thereof, and also has active sites for activating active hydrogen inside the three-dimensional network structure and/or on the surface thereof.

The following description will discuss one embodiment of the present invention in detail.

The activation method for active-hydrogen-containing compounds of the present invention is a method for activating active hydrogen of an active-hydrogen-containing compound by using a polymer gel as an activation catalyst (hereinafter, referred to, simply, as catalyst).

The polymer gel used in the present invention refers to a swelled matter of high polymer compounds having a state in which individual high polymer compounds (for example, compounds having molecular weights of not less than 1,000), which are insoluble to a solvent, absorb the solvent and are completely dispersed in the solvent. Although not particularly limited, the polymer gel used in the present invention is preferably provided as a crosslinking polymer gel having a three-dimensional network structure holding solvent from the viewpoint of catalyst activities and strength, and it is preferable for the polymer gel to have active sites inside the three-dimensional network structure and/or on the surface thereof. Moreover, it is preferable for the above-mentioned polymer gel as a catalyst virtually not to react with the reaction substrate and the solvent.

The above-mentioned polymer gel has an intermediate substance form between a solid and liquid in its gel state holding solvent inside thereof. For this reason, the above-mentioned polymer gel is easily separated and removed from the reaction system after reaction. Moreover, the polymer gel holds the solvent inside its supporting structure, and activates active hydrogen at active sites inside the supporting structure and/or on the surface thereof; thus, it becomes possible to efficiently activate active-hydrogen-containing compounds. In particular, among polymer gels, crosslinking polymer gels which have a three-dimensional network structure holding the solvent, and also have active sites inside the three-dimensional network structure and/or the surface thereof allow easy introduction of the solvent and reaction substrate into the three-dimensional network structure, and make it possible to provide a higher degree of freedom in active sites as compared with heterogeneous catalysts. Therefore, the application of the crosslinking polymer gel as a catalyst allows active hydrogen in an active-hydrogen-containing compound to be activated on the active sites inside the three-dimensional network structure and on the surface thereof, thereby making it possible to improve the reaction rate and the conversion of the reaction substrate.

The formation method of the above-mentioned polymer gel is not particularly limited, and various formation methods, such as those utilizing covalent bond, Coulomb force, hydrogen bond, coordinate bond, etc., are used; the characteristics thereof vary from viscous liquids to substantially hard solid matters depending on their chemical compositions and various factors.

In the present invention, the above-mentioned polymer gel preferably contains a monomer having at least either one of an acidic functional group and a basic functional group as its polymerization unit. With respect to the acidic functional group possessed by the polymer gel, that is, the acidic functional group possessed by the polymer (high polymer compound) in the polymer gel, specific examples include carboxylic group, thiocarboxylic group, sulfonate group, phosphate group, phosphite group, hydroxyl group, phenolic hydroxyl group, thiol group, thiophenolic thiol group, etc. Among the acidic functional groups as exemplified above, carboxyl group, sulfonate group, phosphate group, phosphite group and hydroxyl group are preferably used. Here, the above-mentioned acidic functional groups include esters of acids with their hydrogen atoms in the acidic functional group being substituted by hydrocarbons, and salts of acids being substituted by metal ions.

Moreover, with respect to the basic functional group possessed by the polymer gel, that is, the basic functional group possessed by the polymer (high polymer compound) in the polymer gel, specific examples include functional groups, such as cyano group, isocyano group, thiocyano group and isothiocyano group; functional groups derived from basic compounds, such as amines, amides, thioamides, and heterocyclic compounds (for example, pyrroles, thiophenes, imidazoles, pyrrolidines, piperazines, pyperadines, oxazoles, pyrimidines, pyrazines, pyridazines, purines, thiazoles, pyrazoles, pyridines, carbazoles, etc.), and quaternary salts having one hydrogen ion added to the above-mentioned basic compounds. Among the above-mentioned basic functional groups, those functional groups derived from amines and sulfides (each including cyclic compounds) are preferably used; among these, functional groups derived from at least one kind of basic compound selected from the group consisting of tertiary amine compounds, quaternary ammonium salts, cyclic amine compounds and sulfides are more preferable; among these, functional groups derived from at least one kind of basic compound selected from the group consisting of tertiary amine compounds, quaternary ammonium salts, cyclic amine compounds (especially, pyridines and carbazoles) and thiophenes are still more preferable; and among these, functional groups (cyclic amino group) derived from cyclic amine compounds are most preferable. Moreover, the above-mentioned polymer gel may have a plurality of kinds of basic functional groups.

In accordance with the present invention, since the above-mentioned polymer gel has at least either one of an acidic functional group and a basic functional group, it is possible to carry out a reaction having high selectivity.

In particular, there are a large number of important reactions using the so-called basic reaction system in which reactions proceed through a catalyst having a basic functional group, and since basic catalysts are utilized so as to improve the quality and economy, regardless of whether it is a homogeneous or heterogeneous catalyst, it is highly preferable for the polymer gel to have a basic functional group. The application of the above-mentioned polymer gel having a basic functional group as a catalyst makes it possible to easily introduce a solvent and a reaction substrate into the inside of the gel, and also to provide a higher degree of freedom of active sites as compared with a conventional catalyst having a basic functional group; therefore, since the compound having active hydrogen is activated efficiently, it is possible to improve the reaction rate and consequently to carry out the reaction using the basic reaction system with a higher reaction rate and a higher invert ratio as compared with a conventional system.

Moreover, by allowing the polymer gel to contain both an acidic functional group and a basic functional group so as to have both acid sites and basic sites, it becomes possible to carry out a higher selective reaction with both of the active sites functioning cooperatively.

The polymer gel having a polymer having at least one of an acidic functional group and a basic functional group as a polymerization unit is easily obtained as follows: A monomer having the acidic functional group or basic functional group is polymerized solely, or a monomer having the acidic functional group or basic functional group is copolymerized together with a copolymerizable monomer that can be copolymerized with the monomer having an acidic functional group or a basic functional group, and then the resulting high polymer compound is allowed to absorb a solvent.

The above-mentioned monomer having an acidic functional group is not specifically limited; and for example, a monomer based on a carboxylic acid such as a monomer represented by the following formula (1):

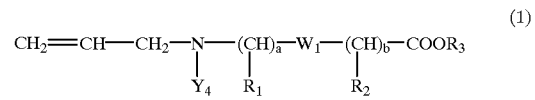

(1)

(In the formula, $Y_4$ represents a hydrogen atom, an allyl group or a $-(CHR_4)_c-W_2-(CHR_5)_d-COOR_6$ group, $R_1$, $R_2$, $R_3$, $R_4$, $R_5$ and $R_6$ individually represent a hydrogen atom or an alkyl group having from 1 to 6 carbon atoms, $W_1$ and $W_2$ individually represent a $-NH-$ group, a $-S-$ group or a $-O-$ group, and a, b, c and d individually represent an integer from 0 to 6.), and (metha) acrylic acid, maleic acid and fumaric acid, is listed.

The above-mentioned monomer having a basic functional group is not specifically limited; and specific examples include: amines, such as vinyl pyridines such as 2-vinylpyridines and 4-vinylpyridine, N-vinylcarbazoles, allyl amines such as N-monoallylamines, N,N-diallylamines and N,N,N-triallylamines, 4-(N,N-dialkylamino) alkylstyrenes, 6-(N-propenylamino)-4-thiahexanoic acid, 6-(N,N-dipropenylamino)-4-thiahexanoic acid, trialkylamine, N,N-dimethylbenzylamine, piperidine, N-alkylpiperidine, pyrrolidine, N-alkylpyrrolidine, piperazine, 2-pyrolidone, imidazole, pyrazole, pyridine, pyrazine, pyrimidine, pyridazine, isoxazole, thiazole, alkylthiazole, quinoline, indole, purine, hexamethyleneimine, 4-dimethylaminopyridine, 1,3,5-triazine, and 2,2,6,6-tetramethyl-4-piperidinol. Among these, tertiary amine compounds and cyclic amine compounds are preferably used; and quaternary ammonium salts; sulfides, such as thiophene, tetra-hydrothiophene, diethylenesulfide, pentamethylenesulfide, 1,3-dithian and 1,4-dithian, are used.

With respect to the above-mentioned copolymerizable monomer, it is not specifically limited, and any monomer that has an olefin group and contains neither an acidic functional group nor a basic functional group may be used. More specifically, the copolymerizable monomer includes, for example, styrene, ethylene, vinylethers, divinylethers, etc. One kind of these copolymerizable monomer may be used, or an appropriate mixture of two or more kinds of these may be used. Here, the ratio of use of the above-mentioned monomer having an acidic functional group or a basic functional group and the copolymerizable monomer is not specifically limited.

The manufacturing method of the above-mentioned high polymer compound, that is, the polymerization method of the monomer component containing the monomer having an acidic functional group or a basic functional group, is not particularly limited; for example, various conventional methods, such as a solution polymerization method, a suspension polymerization method and reverse-phase suspension polymerization method, can be adopted. With respect to a solvent used for polymerizing the monomer component, specific examples are water, toluene, cyclohexane, etc.; however, this is not particularly limited. Moreover, with respect to the suspending agent used for carrying out the suspension polymerization, specific examples are gelatin, dextrin, polyvinylalcohol, sorbitan esters, etc.; however, this is not particularly limited. Additionally, the amounts of use of the above-mentioned solvent and suspending agent are not specifically limited.

Upon polymerizing the above-mentioned monomer component, a polymerization initiator may be used. As for the polymerization initiator, for example, the following radical polymerization initiators, etc. are used: peroxides such as hydrogen peroxide, benzoylperoxide, cumenehydroperoxide; azo compounds such as 2,2'-azobisisobutyronitrile, 2,2'-azobis(2-amidinopropane) dihydrochloride; persulfates such as ammonium persulfate, sodium persulfate, and potassium persulfate. These polymerization initiators may be used alone, or two or more kinds of these may be used in combination. Moreover, instead of using the above-mentioned polymerization initiators, irradiation of radioactive rays, electronic rays, ultraviolet rays, etc. may be used, or the polymerization initiator and the irradiation of radioactive rays, electronic rays, ultraviolet rays, etc. may be used in combination. Here, the amount of use of the above-mentioned polymerization initiator is not specifically limited.

The reaction temperature at the time of the polymerization reaction is appropriately set in accordance with the kinds, etc, of the monomer component and the solvent, and is not particularly limited. Moreover, the time of reaction may be appropriately set in accordance with the kinds and combination, the amount of use, etc. of the reaction temperature, the monomer component, the polymerization initiator, the solvent, etc. Furthermore, the reaction pressure is not particularly limited, and any of the states of normal pressure (atmospheric pressure), reduced pressure and applied pressure, may be used.

Upon carrying out the above-mentioned polymerization reaction, the degree of crosslinking of the resultant crosslinking high polymer is controlled by using a crosslinking monomer (crosslinking agent). With respect to the crosslinking agent, for example, trimethylolpropanetriacrylate, polyethyleneglycoldiacrylate, methylenebisacrylamide, divinylbenzene, etc., are listed; however, this is not particularly limited.

The degree of crosslinking of the above-mentioned crosslinking polymer gel is represented by the molar fraction of a crosslinking agent in the monomer component used for the material of the above-mentioned crosslinking high polymer; normally, it is preferably set in the range of 0.1 mole % to 30 mole %, more preferably, 0.1 mole % to 10 mole %, and most preferably, 0.1 mole a to 5 mole %.

Moreover, with respect to the production method for the high polymer compound of the present invention, the following method may be adopted: After allowing a polymer having a side chain of the primary, or secondary alkyl halogen or sulfonate to react with various sulfidizing agents, the resultant intermediate product is reduced by hydrolysis, processing agents, etc., so as to generate a —SH— group at the end of the polymer, and to this polymer is added unsaturated carboxylic acid such as acrylic acid and methacrylic acid.

For example, with respect to the polymer obtained by the above-mentioned polymerization reaction, that is, the high polymer compound is either a crosslinking high polymer with a substitutional group having a structure represented by the following formula (2):

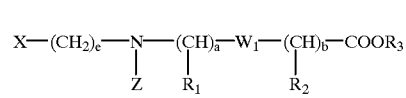

(2)

(in the formula, Z represents a —(CHR$_4$)$_c$—W$_2$—(CHR$_5$)$_d$—COOR$_6$ group, a —(CH$_2$)$_f$—X group, or a hydrogen atom, R$_1$, R$_2$, R$_3$, R$_4$, R$_5$ and R$_6$ individually represent a hydrogen atom or an alkyl group having from 1 to 6 carbon atoms, W$_1$ and W$_2$ individually represent a —NH— group, a —S— group or an —O— group, X represents a polymer main body of carboxylic acid type, and a, b, c, d, e and f individually represent an integer from 0 to 6); or a crosslinking high polymer with a functional group having a structure represented by the following formula (3):

(3)

(in the formula, X represents a polymer main body of carboxylic acid type, and n4 as well as m4 represents an integer from 0 to 6); or a crosslinking high polymer with a substitutional group having at least-one structure selected from the group consisting of: a structure represented by the following formula (4):

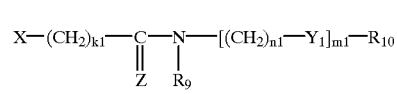

(4)

(in the formula, R$_9$ and R$_{10}$ individually represent a hydrogen atom, a hydrogen carbide group having from 1 to 5 carbon atoms, or a —$(CH_2)_{p1}$—X group, p1 represents an integer from 0 to 6, k1 represents an integer from 0 to 6, m1 represents an integer from 0 to 6, n1 represents an integer from 0 to 6, $Y_1$ represents an —O— group, a —S— group, or a —$NR_{11}$— group, $R_{11}$ represents a hydrogen atom or hydrogen carbide having from 1 to 5 carbon atoms, and X represents a polymer main body of carboxylic acid type), a crosslinking high polymer with a functional group having a structure represented by the following formula (5):

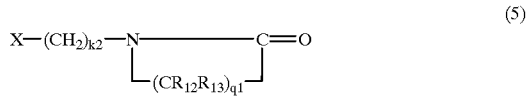

(5)

(in the formula, $R_{12}$ and $R_{13}$ individually represent a hydrogen atom or a hydrocarbon radical having from 1 to 5 carbon atoms, k2 represents an integer from 0 to 6, and q1 represents an integer from 0 to 6), a structure represented by the following formula (6):

(6)

(in the formula, $R_{14}$ represents a hydrogen atom, a hydrocarbon radical having from 1 to 5 carbon atoms, or —$(CH_2)_{p2}$—X group, p2 represents an integer from 0 to 6, $R_{15}$ represents a hydrocarbon radical having from 1 to 5 carbon atoms, or —$(CH_2)_{p3}$—X group, P3 represents an integer from 0 to 6, k3 represents an integer from 0 to 6, and X represents a polymer main body of carboxylic acid type), a structure represented by the following formula (7):

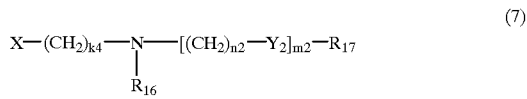

(7)

(in the formula, $R_{16}$ represents a hydrogen atom, a hydrocarbon radical having from 1 to 5 carbon atoms, or —$(CH_2)_{p4}$—X group, p4 represents an integer from 0 to 6, $k_4$ represents an integer from 0 to 6, n2 represents an integer from 1 to 6, $Y_2$ represents an —O— group, an —S— group, an —$NR_{18}$— group or a —$CH_2$-group, $R_{18}$ represents a hydrogen atom, or a hydrocarbon radical having from 1 to 5 carbon atoms, X represents a polymer main body of carboxylic acid type, and m2 represents an integer from 0 to 6, where when m2≠0, $R_{17}$ represents a hydrogen atom, a hydrocarbon radical having from 1 to 5 carbon atoms, a —$(CH_2)_{p5}$—X group, or a Brønsted acid residual group, and when m2=0, it represents a hydrogen atom, a hydrogen carbide group having from 1 to 5 carbon atoms, or a —$(CH_2)_{p5}$—X group, and p5 represents an integer from 0 to 6), and a structure represented by the following formula (8):

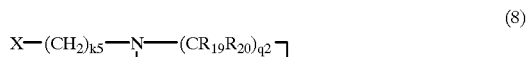

(8)

(in the formula, $R_{19}$ and $R_{20}$ individually represents a hydrogen atom or a hydrocarbon radical having from 1 to 5 carbon atoms, k5 represents an integer from 0 to 6, $q_2$ represents an integer from 4 to 7, and X represents a polymer main body of carboxylic acid type). However, the crosslinking high polymer is not specifically limited, as long as it is insoluble to the solvent and has a three-dimensional network structure, and kinds of the functional group also are not particularly limited.

Here, in the above-mentioned formulas (2) through (8), the polymer main body of carboxylic acid type refers to a main chain of the polymer of carboxylic acid type; and this may be obtained by homopolymerization of a monomer containing a carboxyl group (for example, the above-mentioned monomer of carboxylic acid type), or may be obtained by copolymerization between a monomer containing a carboxyl group and another monomer copolymerizable with the monomer containing a carboxyl group.

Among various high molecular compounds used in the present invention, grainy high molecular compounds, which have a cyclic amine structure and contain a nitrogen atom in the cyclic structure with basic properties, exhibit particularly high basic catalyst performances, and are less susceptible to desorption of the basic functional group containing a nitrogen atom, thereby providing superior heat resistant resins. For this reason, the high molecular compounds of this type are particularly preferable, since they exhibit high basic catalyst performances, are less susceptible to desorption of the basic functional group containing a nitrogen atom, and provide polymer gel having superior heat resistance.

In other words, ion exchange resins such as basic ion exchange resins, which have been generally known as basic resins conventionally, have catalyst functions, etc. as an acid or a base, and exhibit the following advantages as solid-type catalysts, which makes them distinct from normal homogeneous catalysts, (1) easy separation, (2) easy recycling and reuse, (3) easy handling without corrosiveness and (4) no need for waste liquid processing and waste water treatment; moreover, depending on reactions, the high molecular compound serving as a matrix (5) increases the reactivity of the reaction agent, and (6) suppresses undesired side reactions so that the selectivity of the main reaction is enhanced.

However, although the conventional ion exchange resins have the above-mentioned advantages, they are inferior in heat resistance, have limited service conditions, and tend to deteriorate upon application of heat even under their heat resistant temperature (applicable temperature), with the result that their exchange groups are separated and their activity is lowered.

In particular, the commonly known basic ion exchange resins have normally low heat resistant temperatures (applicable temperature) ranging from 40° C. to 60° C., thereby providing only limited service temperatures in terms of industrial use.

However, there are many important reactions using the so-called basic reaction system in which reactions are carried out by using basic resins having a basic functional group as described above. For this reason, there have been ever-increasing demands for polymer gels which have high heat resistant temperatures and are less susceptible to deterioration by heat.

As for the grainy heat-resistant resins having a cyclic amine structure in their main chain, one example is a compound having a polymerization unit (structural unit) represented by the following formula (9):

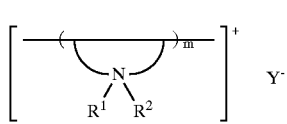

(9)

(in the formula, $R^1$ and $R^2$ individually represent an organic residual group or another polymerization unit, m represents a natural number, and $Y^-$ represents an anion).

The number of carbon atoms within the cyclic amine structure possessed by the above-mentioned heat-resistant resin, that is, the number of carbon atoms in the polymerization unit indicated by the above-mentioned formula (9), is preferably set in the range of 3 to 7, and it is preferable to form 4 to 8 membered ring including nitrogen atoms. Moreover, the organic residual group is exemplified by an alkyl group having from 1 to 6 carbon atoms, etc.

In the above-mentioned formula (9), specific examples of the anion represented by $Y^-$ include ions of halogenides, sulfates, sulfonates, phosphates, hydroxides, borates, cyanides, carbonates, thiocyanates, isocyanates, sulfides, cyanates, acetates, etc.; however, it is not limited by these, and other inorganic ions or organic ions may be used.

Here, the structure of the above-mentioned grainy heat-resistant resin having the above-mentioned cyclic amine structure of the present invention is not intended to be limited by the above-mentioned structure.

The method for obtaining the above-mentioned heat-resistant resin used for the material for the polymer gel of the present invention is not specifically limited, and, for example, various methods may be used in which a monomer component containing a monomer that contains a nitrogen atom in its molecule and is cyclopolymerizable is subjected to cyclopolymerization by using a predetermined method, and in which a monomer component containing a monomer that contains a cyclic amine structure and has a polymerizable functional group is subjected to polymerization by using a predetermined method.

With respect to the cyclopolymerizable monomer, in general, non-conjugate divinyl compounds, etc. have been known. For example, diallyldimethylammoniumchloride undergoes cyclopolymerization to form a polymer having a five-membered ring or six-membered ring structure. Here, in the present invention, the cyclopolymerization refers to a polymerization reaction in which a polymer is formed while ring formation is being carried out during the polymerization.

The above-mentioned cyclopolymerizable monomer used in the present invention, that is, a monomer (polymerizable monomer) that contains a nitrogen atom in its molecule and is cyclopolymerizable, is not particularly limited; and, for example, a monomer having a structure represented by the following formula (10) or (11) may be used:

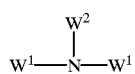

(10)

(in the formula, $W^1$ represents a $-(CH_2)_n-CH=CH_2$ group, $W^2$ represents a hydrogen atom, a $-(CH_2)_n-CH=CH_2$ group, or an alkyl group having from 1 to 6 carbon atoms, and n represents an integer from 0 to 2), or

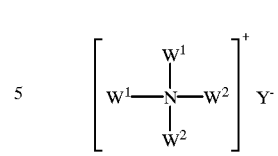

(11)

(in the formula, $W^1$ represents a $-(CH_2)_n-CH=CH_2$ group, $W^2$ represents a hydrogen atom, a $-(CH_2)_n-CH=CH_2$ group, or an alkyl group having from 1 to 6 carbon atoms, n represents an integer from 0 to 2, and $Y^-$ represents an anion).

In the above-mentioned formula (10), specific examples of the anion represented by $Y^-$ include ions of halogenides, sulfates, sulfonates, phosphates, hydroxides, borates, cyanides, carbonates, thiocyanates, isocyanates, sulfides, cyanates, acetates, etc.; however, it is not limited by these, and other inorganic ions or organic ions may be used.

The monomer having the construction represented by the above-mentioned formula (10) or (11) is not particularly limited; and specific examples thereof include diallylamine or its hydrochloride, N,N,N-triallylamines or its hydrochloride, N,N-diallyldimethylammoniumchloride, etc.

Moreover, with respect to the monomer (polymerizable monomer) having a cyclic amine structure and a polymerizable functional group, specific examples include: N-vinylcarbazole, piperidine, N-alkylpiperidine, pyrrolidine, N-alkylpyrrolidine, piperazine, 2-pyrrolidone, imidazole, pyrazole, pyridine, pyrazine, pyrimidine, pyridazine, isoxazole, thiazole, alkylthiazole, quinoline, indole, purine, hexamethyleneimine, 4-dimethylaminopyridine, 1,3,5-triazine, and 2,2,6,6-tetramethyl-4-piperidinol; however, it is not particularly limited by these. One kind of these polymerizable monomers may be used, or two kinds or more of them may be used in combination.

The above-mentioned monomer component used in the present invention may contain a copolymerizable monomer that is copolymerizable with the above-mentioned polymerizable monomer, if necessary, as long as it is used in a range so as not to interfere with the performances of a resultant heat resistant resin. Specific examples of this copolymerizable monomer include styrene, ethylene, vinylethers, etc. One kind of these copolymerizable monomers may be used, or two or more kinds of them may be used in combination, if necessary. Here, the ratio of use of the polymerizable monomer and the copolymerizable monomer is not specifically limited.

Moreover, with respect to the polymerization method, that is, the production method of the grainy heat resistant resin having a cyclic amine structure, various methods may be used in which: for example, the above-mentioned monomer component is subjected to suspension polymerization, or the above-mentioned monomer component is subjected to bulk polymerization and the resultant resin is pulverized.

Among these methods, it is preferable to adopt a method in which a monomer component containing a monomer that contains a nitrogen in its molecule and is cyclopolymerizable, that is, in particular, a monomer component that contains a monomer having a structure represented by the above-mentioned formula (10) or (11), is subjected to suspension polymerization; this method makes it possible to provide a grainy heat resistant resin, which is superior in heat resistance, exhibits a high processing capability as a catalyst, and has a spherical shape (pearl shape) having a predetermined particle size.

The reaction conditions at the time of carrying out the above-mentioned polymerization reaction are not particularly limited; and with respect to a solvent, a suspension agent, a polymerization initiator, etc. used in the polymerization reaction, those solvent, suspension agent, polymerization initiator, etc. as described earlier may be used.

Even in the case when the high molecular compound used in the present invention is a grainy heat resistant resin having a cyclic amine structure, it is preferable that the heat resistant resin is insoluble to the solvent and can be separated so as to serve as a catalyst. Therefore, the above-mentioned heat resistant resin is preferably provided as a crosslinking high polymer having a crosslinking structure.

The type of formation of crosslinking structure of the above-mentioned heat resistant resin is not particularly limited, and various formation methods, such as, for example, those utilizing covalent bond, Coulomb force, hydrogen bond, coordinate bond, etc., are used. Among these, the formation of crosslinking structure utilizing covalent bond is more preferably used.

Upon polymerizing the above-mentioned monomer component, a crosslinking monomer (crosslinking agent) is used, if necessary. As for the crosslinking agent, for example, the aforementioned crosslinking agents may be used, and the amount of use of the crosslinking agent may be determined so that the degree of crosslinking of the heat resistant resin is set to the aforementioned degree of crosslinking.

The above-mentioned heat resistant resin can be obtained easily as follows: after the suspension polymerization, the resultant polymer (polymer beads) is filtered and taken out, and sufficiently washed by a solvent, if necessary, and then dried by using a known method, such as using an evaporator or a vacuum drying process.

Moreover, for example, in the case of application of the bulk polymerization method as the production method of the heat resistant resin, the grainy heat resistant resin of the present invention can be obtained by pulverizing the resultant polymer.

In other words, in the present invention, not limited to a globular shape, that is, a spherical shape or a round shape, the particle shape includes an elliptical shape, a rectangular shape, or irregular crushed shapes, etc., as long as the particle size is small to a certain degree.

As described above, the particle shape of the heat resistant resin of the present invention may have irregular crushed shapes obtained through the pulverizing process, or may have a spherical shape obtained through the suspension polymerization; however, the spherical shape (pearl shape) obtained through the suspension polymerization is more preferable since the effects of the present invention are exerted more remarkably.

Moreover, although not particularly limited, the average particle size of the above-mentioned heat resistant resin is preferably set in the range of 0.2 mm to 2 mm, and more preferably, 0.42 mm to 1.18 mm, in terms of the industrial use. The average particle size of less than 0.2 mm tends to make the separating operation after the reaction more difficult when the heat resistant resin is used as a catalyst. The average particle size exceeding 2 mm of the heat resistant resin requires more time to allow the material or the reaction product to be dispersed inside the resin when the heat resistant resin is used as a catalyst, thereby failing to provide a proper application.

In other words, the thermal decomposition temperature of the grainy heat resistant resin having a cyclic amine structure is not less than 300° C., and more preferably, not less than 390° C.; therefore, it is greatly superior in thermal stability. Consequently, the above-mentioned heat resistant resin is applicable under high temperatures, and there is no limitation to the conditions in which the heat resistant resin exhibits its basic catalyst performance. Moreover, since the heat resistant resin has a cyclic amine structure, the basic catalyst performance is high, and it is less susceptible to desorption of the basic functional group containing a nitrogen atom, and hardly deteriorates even upon heat application. Moreover, it also has superior chemical resistance. For this reason, the heat resistant resin is less susceptible to elution of nitrogen atoms that form a factor of the functionality, thereby making it possible to prevent reduction in the activity due to elution of nitrogen atoms. Therefore, the above-mentioned heat resistant resin exerts a high processing capability as a catalyst, and hardly deteriorate even upon heat application (heat deterioration); thus, it can be repeatedly used stably for a long time, and is very advantageous in cost reduction.

Therefore, the above-mentioned heat resistant resin is preferably used for a high molecular resin that constitutes the polymer gel in accordance with the present invention.

The polymer gel used in the present invention can be easily obtained by the following method: The resultant polymer (high molecular compound), obtained by any of the above-mentioned various polymerization reactions, is filtered and sufficiently washed by a solvent, and then dried by a known method such as using an evaporator or a vacuum drying process. Then, this is allowed to absorb and maintain a solvent having an affinity to the high molecular compound. Moreover, the above-mentioned polymer gel may be directly obtained from the polymerization reaction by appropriately setting the polymerization conditions.

The above-mentioned polymer gel used in the present invention is preferably set so as to have a ratio of swelling of not less than 2. The ratio of swelling of the polymer gel refers to a ratio of the volume of the above-mentioned polymer gel to the volume of the high molecular compound that is obtained by drying the polymer gel, which is a scale indicating how many times the volume of the high molecular compound has increased to by absorbing the solvent. In the present invention, the ratio of swelling of the polymer gel is set to at least not less than 2; however, it is more preferable to set the ratio in the range of 2 to 10 in order to maintain the shape-retaining property of the gel and to further simplify the separation and removing operations after the reaction. Moreover, in order to further enhance the degree of freedom of active sites that the polymer gel possesses, to stimulate the introduction of the reaction solution (solvent) into the inside of the gel, and to allow the gel to exert its catalytic activity sufficiently, the ratio of swelling of the polymer gel is more preferably set in the range of 2.5 to 10, and most preferably, 3 to 8.

In the present invention, the solvent that is held by the polymer gel is not specifically limited, and the solvent applied to the reaction using the above-mentioned polymer gel may be used, or the reaction substrate (active-hydrogen-containing compound) itself may be used. In other words, the above-mentioned polymer gel may be added to the reaction system in a gel state that has been preliminarily formed, or may be formed in the reaction system in which the high molecular compound before formation of the gel is added to the reaction system, and mixed, and then allowed to absorb the solvent used in the reaction or the reaction substrate itself so as to be swelled. In either of the cases, when the polymer gel is used as a catalyst, the activation of the active hydrogen possessed by the active-hydrogencontaining composition explosively from the time when the high molecular compound starts forming the gel. Therefore, in the case when the polymer gel is used as a catalyst, it is more preferable that the polymer gel has already formed the gel at the time of addition to the reaction system. In this manner, the polymer gel, which contains an active-hydrogen-containing compound having active hydrogen to be activated, readily allows the active hydrogen to be activated in the active-hydrogen-containing compound, when added to a desired reaction system in which the active hydrogen is activated.

The above-mentioned polymer gel as it is may be used as a catalyst, or may be used by having a metal deposited thereon, if necessary. Specific examples of this metal include copper, lead, nickel, zinc, iron, cobalt, chromium, manganese, bismuth, tin, antimony, alkali earth metals, etc; however, it is not particularly limited.

In the case when a metal is deposited on the polymer gel, the amount of the metal to the high molecular compound is not particularly limited, and is appropriately set depending on the kind of a high molecular compound, the kind of a synthesis reaction to be applied, etc. Here, the deposition is carried out in forms such as salt, adsorption and amplexus, in addition to chelate; however, the form of the deposition is not particularly limited. Moreover, the metal to be deposited may be applied as ions or as metal it is. Here, with respect to the form of the ions, oxides, halogenides, sulfides, etc. may be exemplified.

In the present invention, the active hydrogen to be activated refers to hydrogen atoms that relate to a desired reaction among all the hydrogen atoms that a compound in question possesses. Therefore, although not particularly limited, the above-mentioned active hydrogen is preferably provided as hydrogen atoms that are more reactive than hydrogen atoms that are directly bonded to carbon atoms in an organic compound that has no hetero atoms. Specific examples of the above-mentioned active hydrogen include hydrogen atoms directly bonded to hetero atoms; hydrogen atoms ($\alpha$-hydrogen atoms) bonded to carbon atoms adjacent to an electron attracting group; hydrogen atoms constituting a substituted aromatic compound; and hydrogen atoms constituting a functional group of aldehyde and carboxylic acid. Moreover, with respect to the hydrogen atoms directly bonded to the hetero atom, specific examples include hydrogen atoms constituting a functional group, such as an —$NH_2$ group, a —CONH group, an —OH group and an —SH group. Moreover, with respect to the hydrogen atoms bonded to carbon atoms adjacent to an electron attracting group, specific examples include a hydrogen atom at the $\alpha$ position of a carbonyl compound, etc.

Therefore, the active-hydrogen-containing compound of the present invention refers to a compound having such active hydrogen. Among active-hydrogen-containing compounds, unsaturated carboxylic acids are preferably used, and among unsaturated carboxylic acids, (metha) acrylic acid is most preferably used. Moreover, in the case when the active-hydrogen-containing compound has a plurality of kinds of active hydrogen, these kinds of active hydrogen may be mutually the same, or different from each other.

In the present invention, the activation of the active-hydrogen-containing compound means to draw the active hydrogen (or make it easier to be dissociated), that is, to activate the active hydrogen contained in the active-hydrogen-containing compound. In other words, the above-mentioned polymer gel is preferably applied to various reactions relating to activation of the active hydrogen in which the active hydrogen is drawn from the active-hydrogen-containing compound, or the active hydrogen is made easier to be dissociated so that nucleophilic addition is carried out.

The following description will discuss examples of reaction in which activation of the active-hydrogen-containing compound is carried out and to which the polymer gel of the present invention is applicable, that is, various examples of reaction in which activation of the active-hydrogen-containing compound is carried out and the polymer gel is preferably used as a catalyst. Here, in the following examples of reaction only give some cases to which the polymer gel is applicable, and the present invention is not intended to be limited thereby. Additionally, in the following examples of reaction (reaction formulas), R, $R^1$ and $R^2$ individually represent a hydrogen atom or an organic residual group, such as an alkyl group, Ar represents an aryl group, X represents a halogen atom, such as F, Cl, Br and I, and A represents O, S, or NH.

With respect to reactions in which a hydrogen atom directly bonded to a hetero atom is allowed to react, for example, the following reactions are listed: addition reactions of a heterocyclic compound (for example, ethylene oxide, ethylene imine, ethylene sulfide, etc.) to amines (first amines or second amines), which are, for example, represented by the following reaction examples (reaction formulas):

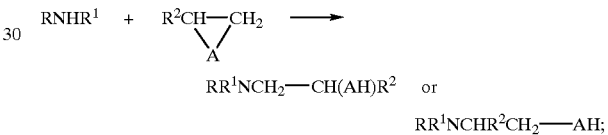

conversion reactions from amines (first amines and second amines) to amides represented by the following reaction examples:

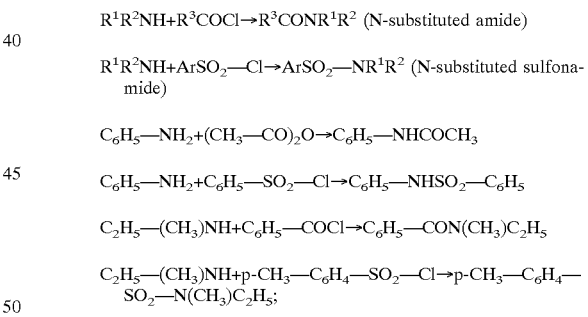

hydrolysis reactions of amides represented by the following reaction example:

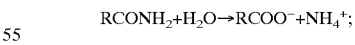

Addition reactions of a heterocyclic compound to amides represented by the following reaction example, and more specifically, addition reaction of ethylene oxide to pyrrolidine or isocyanuric acid:

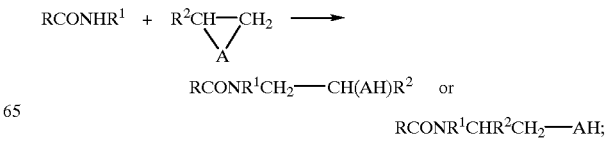

Addition reactions of a heterocyclic compound to thioamides represented by the following reaction example:

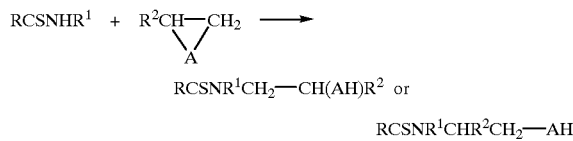

RCSNR¹CH₂—CH(AH)R² or

RCSNR¹CHR²CH₂—AH

Addition reactions of a heterocyclic compound to alcohols (primary alcohols, secondary alcohols, or tertiary alcohols) represented by the following reaction example, and more specifically, addition reactions of an oxirane compound, such as ethylene oxide and propylene oxide, to methanol, ethanol, propanol or butanol:

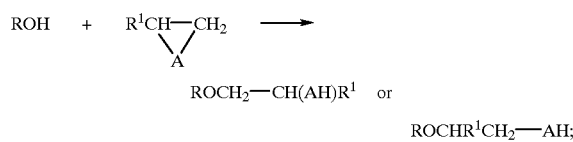

ROCH₂—CH(AH)R¹  or

ROCHR¹CH₂—AH;

Reactions between alcohols (primary alcohols, secondary alcohols, or tertiary alcohols) and hydrogen halide represented by the following reaction examples, and more specifically, for example, the following reaction in which isopropyl bromide is synthesized from isopropyl alcohol and concentrated hydrogen bromide:

ROH+HX→RX+H₂O (CH₃)₂CHOH+HBr→(CH₃)₂CHBr+H₂O;

Synthesizing reactions of ester using alcohols (primary alcohols, secondary alcohols, or tertiary alcohols) represented by the following reaction examples:

ROH+p-CH₃—C₆H₄—SO₂—Cl (p-toluenesulfonyl chloride)→p-CH₃—C₆H₄—SO₂—OR (alkyltosylate)

ROH+R¹COOH→R¹COOR+H₂O;

Oxidation reactions of alcohols (primary alcohols, secondary alcohols, or tertiary alcohols) represented by the following reaction example:

RR¹CHOH+(½)O₂→RR¹CO+H₂O

Addition reactions of a heterocyclic compound to phenols (more specifically, phenol, hydroquinone, bisphenol A, bisphenol F, bisphenol S, BHPF (bishydroxyphenylfluorene), dihydroxydiphenylmethane, etc. represented by the following reaction examples:

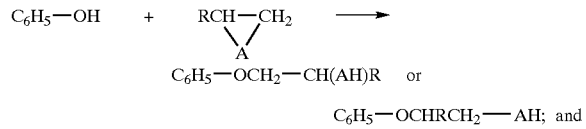

C₆H₅—OCH₂—CH(AH)R   or

C₆H₅—OCHRCH₂—AH; and

Reactions (Williamson synthesizing reaction) for synthesizing ethers from phenols and alkyl halides represented by the following reaction examples, and more specifically, the following reaction in which p-nitrobenzyl-p-tolylether is synthesized from, for example, p-cresol and p-nitrobenzyl bromide:

C₆H₅—OH+RX→C₆H₅—OR p-CH₃—C₆CH₄—OH+p-BrCH₂—C₆H₄—NO₂ (p-cresol) (p-nitrobenzylbromide)→p-CH₃—C₆H₄—O-(p-CH₂—C₆H₄—NO₂); (p-nitrobenzyl-p-tolylether)

synthesizing reactions of ester using phenols represented by the following reactions, and more specifically, for example, the following reactions in which p-nitrophenyl acetate is synthesized from p-nitrophenol and acetate anhydride and in which o-bromophenyl-p-toluenesulfonate is synthesized from o-bromophenol and p-toluenesulfonyl chloride:

C₆H₅—OH+RCOCl→RCOOC₆H₅ p-NO₂—C₆H₄—OH+(CH₃—CO)₂O (p-nitrophenol) (acetate anhydride)→p-NO₂—C₆H₄—OCOCH₃ (p-nitrophenylacetate)

o-Br—C₆H₄—OH+p-CH₃—C₆H₄—SO₂—Cl (o-bromophenol) (p-toluenesulfonyl chloride)→p-CH₃—C₆H₄—SO₂—O-(o-Br—C₆H₄) (o-bromophenyl-p-toluenesulfonate);

addition reactions of a heterocyclic compound to thiols (more specifically, primary thiol, secondary, thiol or tertiary thiol) represented by the following reaction example:

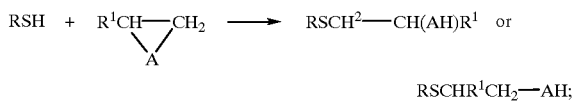

RSCHR¹CH₂—AH;

Addition reactions of a heterocyclic compound to thiophenols represented by the following reaction example:

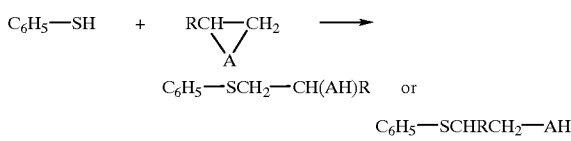

C₆H₅—SCH₂—CH(AH)R   or

C₆H₅—SCHRCH₂—AH

Here, reactions related to a hydrogen atom directly bonded to a hetero atom are not limited only to the above-mentioned reactions.

Moreover, with respect to reactions to which hydrogen atoms bonded to carbon atoms adjacent to an electron attracting group contribute, specific examples include:

halogenation reactions of ketones represented by the following reaction example, and more specifically, for example the following reaction in which bromine atoms are added to cyclohexane.

—CHCO—+X₂→—CXCO—+HX

C₅H₁₀C=O+Br₂→C₅H₉(Br)C=O+HBr; (cyclohexane)

aldol condensation reactions represented by the following reaction examples, and more specifically, for example, the following reactions in which 3-hydroxybutanal is synthesized from acetoaldehyde and in which diacetone alcohol is synthesized from acetone:

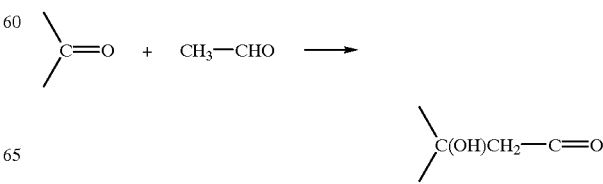

-continued

2 CH$_3$—CHO (acetaldehyde) ⟶ CH$_3$—CH(OH)CH$_2$—CHO; (3-hydroxybutanal)

2 CH$_3$—C(=O)—CH$_3$ (acetone) ⟶ CH$_3$—C(OH)(CH$_3$)—CH$_2$—C(=O)—CH$_3$; (diacetone alcohol)

various nucleophilic addition reactions to carbonyl compounds (ketones) represented by the following reaction examples:

Perkin condensation reaction represented by the following reaction example:

C$_6$H$_5$—CHO+(CH$_3$—CO)$_2$O$_2$→C$_6$H$_3$—CH=CHCOOH;

Knoevenagel condensation reaction represented by the following reaction example:

C$_6$H$_5$—CHO+CH$_2$(COOC$_2$H$_5$)$_2$→C$_6$H$_3$—CH=C(COOC$_2$H$_5$)$_2$;

Cope reaction represented by the following reaction example:

C$_5$H$_{10}$—C=O+N≡C—CH$_2$—COOC$_2$H$_5$→C$_5$H$_{10}$—C=C(CN)COOC$_2$H$_5$;

Wittig reaction represented by the following reaction examples:

>C=O + Ph$_3$P=CRR$^1$ ⟶

>CO$^-$—CRR$^1$—P$^+$Ph$_3$ ⟶

>C=CRR$^1$ + Ph$_3$P=O (C$_6$H$_5$)$_2$CO + Ph$_3$P=CH$_2$ ⟶

(C$_6$H$_5$)$_2$CO$^-$—CH$_2$—P$^+$Ph$_3$ ⟶

(C$_6$H$_5$)$_2$C=CH$_2$ + Ph$_3$P=O nucleophilic acylation reactions to ketones, such as Claisen condensation reaction represented by the following reaction examples:

—COOR+R$^1$CH$_2$—COOR$^2$→—CO—CH$_2$COOR$^2$+R$^1$OR

2 CH$_3$—COOC$_2$H$_5$→CH$_3$—CO—CH$_2$—COOC$_2$H$_5$+C$_2$H$_5$—OH addition reaction (Michael addition reaction) to α, β-unsaturated carbonyl compounds (ketones) represented by the following reaction examples:

CH$_2$=CHCHO+H$_2$O→CH$_2$(OH)CH$_2$—CHO

CH$_2$=C(CH$_3$)COOC$_2$H$_5$+N≡C—CH$_2$—COOC$_2$H$_5$→N≡C—CH(COOC$_2$H$_5$)CH$_2$—CH(CH$_3$)COOC$_2$H$_5$

Here, reactions to which hydrogen atoms bonded to carbon atoms adjacent to an electron attracting group contribute are not limited by the above-mentioned examples.

Moreover, with respect to reactions to which hydrogen atoms constituting a substituted aromatic compound contribute, for example, the following reactions are listed:

Reimer-Tiemann reaction represented by:

C$_6$H$_5$—OH+CHCl$_3$→C$_6$H$_4$(CHCl$_2$)OH+HCl→C$_6$H$_4$(OH)CHO (salicyl aldehyde); and Friedel-Crafts acylation reaction represented by:

C$_6$H$_4$(OH)$_2$+CH$_3$(CH$_2$)$_4$—COOH (resorcinol) (caproic acid)→ C$_6$H$_3$(OH)$_2$—CO(CH$_2$)$_4$—CH$_3$+H$_2$O (2,4-dihydroxyphenyl-n-pentylketone)

However, reactions to which hydrogen atoms constituting a substituted aromatic compound contribute are not limited only to the above-mentioned reaction examples.

Furthermore, with respect to reactions to which hydrogen atoms constituting a functional group of aldehyde, carboxylic acid, etc. contribute, addition reactions of heterocyclic compounds (more specifically, ethylene oxide, propion oxide, etc.) to carboxylic acids (more specifically acrylic acid, methacrylic acid, acetic acid, propionic acid, etc.) represented by the following reaction example, are listed:

RCOOH + R$^1$CH—CH$_2$ (A) ⟶

RCOOCH$_2$—CH(AH)R$^1$ or

RCOOCHR$^1$CH$_2$—AH

More specifically, these reactions include: reactions in which from (metha)acrylic acid and ethylene oxide, (metha) acrylic acid hydroxyethyl ester and (metha)acrylic acid hydroxypropyl ester are synthesized, which are known as important industrial reactions; addition reactions of a heterocyclic compound to thiocarboxylic acids represented by the following:

RCSOH + R$^1$CH—CH$_2$ (A) ⟶ RCSOCH$_2$—CH(AH)R$^1$ or

RCSOCHR$^1$CH$_2$—AH;

addition reactions of alcohol to aldehydes represented by the following reaction example:

CH$_3$—CHO+2 C$_2$H$_5$—OH→CH$_3$—CH(OC$_2$H$_5$)$_2$+H$_2$O; and

Cannizzaro reaction represented by:

2 RCHO+H$_2$O→RCH$_2$OH+RCOOH more specifically, a reaction in which n-butylformaldehyde is aldol condensated by formaldehyde two times, and then subjected to a Cannizzaro reaction so as to obtain trimethylolpropane. Here, the reactions to which hydrogen atoms constituting a functional group of aldehydes, carboxylic acids, etc. are not limited only to the above-mentioned reactions.

Among those reactions accompanying activation of active hydrogen in active-hydrogen-containing compounds, the polymer gel of the present invention is preferably applied to: addition reactions of heterocyclic compounds (preferably, oxirane compounds, and more preferably, ethylene oxide and propylene oxide) or aldehydes to an active-hydrogen-containing compound selected from the group consisting of phenols, amides, alcohols, carboxylic acids, malonic acid, cyano acetic acid and esters thereof; Mannich reaction; alkylation reaction of aromatic compounds; hydroxyalkyl esterification reaction of (metha)acrylic acid disclosed in Japanese Examined Patent Publication 13019/1966 (Tokukoushou 41-13019); cyanohydrin production reaction; cyano ethylation reaction. Among these, it is most preferably applied to addition reactions of oxirane compounds or aldehydes (more preferably, oxirane compounds) to an active-hydrogen-containing compound selected from the group consisting of phenols, amides, alcohols, carboxylic acids, malonic acid, cyano acetic acid and esters thereof (more preferably, to carboxylic acids and esters thereof, and most preferably, (metha)acrylic acid).

As described above, the polymer gel of the present invention is preferably applied to various reactions accompanying activation of active hydrogen in active-hydrogen-containing compounds as a catalyst.

In the present invention, upon carrying out the above-mentioned various reactions accompanying the activation of active hydrogen in active-hydrogen-containing compounds by using the above-mentioned polymer gel as a catalyst, it is preferable to carry out the activation of active hydrogen under the condition that the amount of active sites (reaction active sites) of the polymer gel per unit value in the reaction system accompanying the activation of active hydrogen, especially, the amount of basic active sites, is set to not less than 0.43 mmol/cc.

The amount of the active sites of the polymer gel per unit volume in the reaction system accompanying an activation of active hydrogen is represented by a product between (a) the amount of functional groups per dry unit weight of the above-mentioned high molecular gel, that is, the amount of functional groups (mmol/g) per unit weight of a high molecular compound (polymer) constituting the polymer gel, and (b) the apparent specific gravity (g/cc) of the polymer gel in the reaction system. Therefore, in the present invention, upon carrying out the above-mentioned various reactions accompanying the activation of active hydrogen in active-hydrogen-containing compounds by using the above-mentioned polymer gel as a catalyst, it is preferable to carry out the activation of active hydrogen under the condition that the product between the amount of basic functional groups per dry unit weight of the above-mentioned polymer gel and the apparent specific gravity of the polymer gel in the reaction system accompanying an activation of active hydrogen is set to not less than 0.43 mmol/cc.

The amount of functional groups per unit weight of a high molecular compound constituting the polymer gel can be univocally determined depending on elements constituting the high molecular compound, and can be measured by using a method such as an element analysis.

On the other hand, the apparent specific gravity of polymer gel in the reaction system (in the reaction solution) depends on the synthesizing method of the high molecular compound. In other words, the apparent specific gravity of the polymer gel in the reaction system can be adjusted by improving the degree of crosslinking of the above-mentioned high molecular compound and adjusting the monomer density upon synthesizing the above-mentioned high molecular compound. Therefore, upon synthesizing the high molecular compound, for example, upon suspension polymerization, by adding various cross-linkers to the monomer phase and adjusting the monomer density of the monomer phase, it is possible to increase the apparent specific gravity of the high molecular compound that swelled in the reaction system upon carrying out the various reactions accompanying the activation of active hydrogen, that is, the apparent specific gravity of the polymer gel.

Therefore, in the present invention, upon carrying out the various reactions accompanying the activation of hydrogen by using the above-mentioned polymer gel as a catalyst, it is preferable to change the reaction conditions upon synthesizing the high molecular compound (polymer) depending on the kind of the high molecular compound (polymer) to be use so that the amount of the basic active sites of the polymer gel per unit volume in the reaction system accompanying an activation of active hydrogen is set to not less than 0.43 mmol/cc, or it is preferable to selectively use a polymer gel or a high molecular compound among polymer gels suitable for the reaction or high molecular compounds that swell to form polymer gels, depending on the kind of reaction accompanying an activation of active hydrogen, so that the amount of the basic active sites of the polymer gel per unit volume in the reaction system is set to not less than 0.43 mmol/cc.

In this manner, it is possible to reduce the amount of use of the polymer gel and also to increase the productivity by increasing the active sites of the reaction system, that is, in particular, the density of the basic active sites.

In other words, in order to improve the productivity and quality of the product, the greater the amount of load of the polymer gel as a catalyst, the better; however, the amount of use is limited by the size of the reactor and the stirring force. Therefore, it is essential to prepare a catalyst having a high activity per unit volume.

Moreover, in the reaction using the polymer gel and accompanying an activation of active hydrogen, the reaction rate of the main reaction is by far greater than the reaction rate of the sub reaction. Therefore, the above-mentioned arrangement makes it possible to further improve the selectivity.

The method for separating and removing the above-mentioned polymer gel from the reaction system is not specifically limited, and it is possible to easily separate and remove the high molecular gel from the reaction system by using, for example, a method such as filtration.

As described above, the activation method for an active-hydrogen-containing compound of the present invention is a method in which active hydrogen in the active-hydrogen-containing compound is activated by using a polymer gel as an active catalyst. Moreover, the polymer gel of the present invention, which is used as an activation catalyst for the active-hydrogen-containing compound in the above-mentioned reaction, has a three-dimensional network structure holding a solvent inside thereof, and possesses active sites on the surface of the three-dimensional network structure and the inside thereof. The ratio of swelling of the polymer gel is preferably set to not less than 2.

In the present invention, the polymer gel (activation catalyst), used for the activation method for the active-hydrogen-containing compound, forms a gel with the solvent holding inside thereof, that is, has an intermediate substance form between a solid and liquid; this allows easy separation and removing operations from the reaction system after reaction. Moreover, since the polymer gel (activation catalyst) has the three-dimensional network structure holding the solvent with active sites located on the surface and the inside thereof, it is possible to provide a higher degree of freedom in active sites as compared with heterogeneous catalysts. Furthermore, since the activation of the active-hydrogen-containing compound occurs on the active sites on the surface of the three-dimensional network structure and inside thereof, it is possible to provide superior catalyst activities and consequently to improve the reaction rate and the conversion of the reaction substrate. Thus, by activating active hydrogen in the active-hydrogen-containing compound using the above-mentioned polymer gel, the active-hydrogen-containing compound can be efficiently activated, thereby making it possible to satisfy both the catalyst activities on the reaction rate and conversion of the reaction substrate and the operability related to the separation operation, etc.

In particular, when the polymer gel has a basic functional group, a reaction using the so-called basic reaction system which carries out reactions by using a catalyst having a basic functional group can be performed with a high reaction rate and high conversion. In this case, it is preferable to carry out the activation of active hydrogen in the reaction system accompanying an activation of active hydrogen under the condition that the amount of basic active sites of the polymer gel per unit volume in the reaction system is set to not less than 0.43 mmol/cc, where the amount of basic active sites is represented by a product between the amount of the basic functional group per unit dry weight of the polymer gel and the apparent specific gravity of the above-mentioned polymer gel in the above-mentioned reaction system.

In this manner, it is possible to reduce the amount of use of the polymer gel and also to improve the productivity by increasing the density of the reaction active sites in the reaction system. Moreover, in the reaction using the polymer gel and accompanying an activation of active hydrogen, the reaction rate of the main reaction is by far greater than the reaction rate of the sub reaction. Therefore, the above-mentioned arrangement makes it possible to further improve the selectivity of the reaction product of the main reaction.

Moreover, especially when the above-mentioned polymer gel (activation catalyst) is made of a high molecular compound having a cyclic amine structure in its main chain, it is less susceptible to elution of the basic functional group including nitrogen atoms, less subjected to degradation by heat, and has superior chemical resistance. Therefore, it is possible to prevent reduction in the activity due to elution of nitrogen atoms caused by degradation by heat, etc.

Furthermore, a grainy high molecular compound having a cyclic amine structure in its main chain is particularly superior in its basic catalytic performance, and also has a high heat resistant property, that is, not less than 300 C in thermal decomposition temperature. Therefore, the application of a polymer gel made of the above-mentioned heat resistant resin as a catalyst (activation catalyst) for activating active hydrogen possessed by an active-hydrogen-containing compound makes it possible to provide an activation method of the active-hydrogen-containing compound which allows an easy separation process for the catalyst, is superior in its thermostability, and makes it possible to activate the active-hydrogen-containing compound efficiently for a long time.

The novel features which are considered as characteristic of the invention are set forth in particular in the appended claims. The improved production method and the improved composition will be best understood upon perusal of the following detailed description of certain specific embodiments.

THE BEST MODE FOR CARRYING OUT THE INVENTION

Referring to examples and comparative examples, the following description will discuss the present invention in detail; however the present invention is not intended to be limited thereby. Here, the conversion of the reaction substrate and the selectivity of the reaction product are defined as follows:

> Conversion of reaction substrate (%)=Number of Moles of reaction substrate consumed/Number of moles of supplied reaction substrate×100
>
> Selectivity of reaction product (%)=Number of moles of reaction substrate converted to reaction product/Number of moles of consumed reaction substrate×100

Moreover, the amount of active sites (basic active sites) of the catalyst (polymer gel) per unit volume in the reaction solution is defined as follows:

Amount of active sites of catalyst per unit volume in the reaction solution (mmol/c)=Amount of functional group (basic functional group) per unit weight of polymer (high molecular compound) to form catalyst (polymer gel) (mmol/g)×Apparent specific gravity in reaction solution (g/cc)

Embodiment 1

To a reaction container having a thermometer, a mixer, a titration device and a reflux condenser were loaded 8 kg of cyclohexane serving as a solvent and 60 g of sorbitanmonostearate, and stirred. Next, to this reaction container were added 597 g of a monomer component made of 6-(N,N-dipropenylamino)-4-thiahexanoic acid and acrylic acid, 56 g of trimethylolpropanetriacrylate serving as a cross-linking agent and 751 g of water serving as a solvent and the mixed solution thus obtained was heated to 70° C. Here, the above-mentioned 6-(N,N-dipropenylamino)-4-thiahexanoic acid was added so that the amount of use of 6-(N,N-dipropenylamino)-4-thiahexanic acid in the monomer component is set at 5 mole %. Further, to the titration device was loaded 200 ml of an aqueous solution of 0.4% by weight of 2,2'-azobis(2-amidinopropane) dihydrochloride (manufactured by Wako Pure Chemical Industries corporation; tradename V-50) as a polymerization initiator. Next, the polymerization initiator inside the titration device was dropped into the above-mentioned mixed solution in 20 minutes. Thereafter, the reaction solution inside the reaction container was further stirred for three hours, and then the stirring was stopped. Then, the reaction solution was allowed to stand for one night at room temperature so as to age the reaction. Consequently, a reaction product in the shape of beads having a size of approximately 0.1 mm to 2 mm was obtained.

Thereafter, the reaction product in the shape of beads thus obtained was shifted to a rotary evaporator, and after cyclohexane had been distilled away, this was dried at 80° C. under reduced pressure, thereby obtaining 540 g of polymer (1). Polymer (1) was provided with a functional group having a structure derived from aminothiahexanoic acid. Here, the amount of the basic functional group was 0.6 mmol/g per unit weight of polymer (1).

Thereafter, polymer (1) was dipped into ion exchange water, and allowed to absorb the ion exchange water; thus, a gel, swelled to approximately 4 times per 1 ml of polymer (1), was obtained as a polymer gel (cross-linking polymer gel) in accordance with the present invention (ratio of swell: 4).

Embodiment 2

To a reaction container having a thermometer, a mixer, a titration device and a reflux condenser were loaded 8 kg of cyclohexane serving as a solvent and a fixed amount of suspension agent, and stirred. Next, to this reaction container were added 600 g of a monomer component made of 6-(N,N-dipropenylamino)-4-thiahexanoic acid and acrylic acid, 20 g of trimethylolpropanetriacrylate serving as a cross-linking agent and 600 g of water serving as a solvent, and the mixed solution thus obtained was heated to 70° C. Here, the above-mentioned 6-(N,N-dipropenylamino)-4-thiahexanoic acid was added so that the amount of use of 6-(N,N-dipropenylamino)-4-thiahexanic acid in the monomer component is set at 30 mole %. Meanwhile, to the titration device was loaded a fixed amount of an aqueous solution having a fixed concentration of 2,2'-azobis (2-amidinopropane) dihydrochloride (manufactured by Wako Pure Chemical Industries corporation; tradename V-50) as a polymerization initiator. Next, the polymerization initiator inside the titration device was dropped into the above-mentioned mixed solution in 20 minutes. Thereafter, the reaction solution inside the reaction container was further stirred for three hours, and then the stirring was stopped. Then, the reaction solution was allowed to stand for two hours at room temperature so as to age the reaction. Thereafter, the reaction solution was subjected to a decantation process, washed by a fixed amount of cyclohexane, and then dried at 80° C. under reduced pressure; thus, polymer (2) weighing approximately 440 g was obtained. Here, the amount of the basic functional group was 0.7 mmol/g per unit weight of polymer (2).

Thereafter, polymer (2) was dipped into ion exchange water, and allowed to absorb the ion exchange water; thus, a gel, swelled to approximately 7 times per 1 ml of polymer (2), was obtained as a polymer gel (cross-linking polymer gel) in accordance with the present invention (ratio of swell: 7).

Embodiment 3

To a reaction container having a thermometer, a mixer, a titration device and a reflux condenser were loaded 8 kg of cyclohexane serving as a solvent and a fixed amount of suspension agent, and stirred. Next, to this reaction container were added 580 g of a monomer component made of N,N-diallylamine and acrylic acid, 28 g of trimethylolpropanetriacrylate serving as a cross-linking agent and 2400 g of water serving as a solvent and the mixed solution was heated to 70° C. Here, the above-mentioned N,N-diallylamine was added so that the amount of use of N,N-diallylamine in the monomer component is set at 5 mole %. Further, to the titration device was loaded a fixed amount of an aqueous solution of 2,2'-azobis (2-amidinopropane) dihydrochloride (manufactured by Wako Pure Chemical Industries corporation; tradename V-50) having a predetermined concentration as a polymerization initiator. Next, the polymerization initiator inside the titration device was dropped into the above-mentioned mixed solution in 20 minutes. Thereafter, the reaction solution inside the reaction container was further stirred for three hours, and then the stirring was stopped. Then, the reaction solution was allowed to stand for one night at room temperature so as to age the reaction. Consequently, a reaction product in the shape of beads having a size of approximately 0.1 mm to 2 mm was obtained.

Thereafter, the reaction product in the shape of beads thus obtained was shifted to a rotary evaporator, and after cyclohexane had been distilled away, this was dried at 80° C. under reduced pressure, thereby obtaining 600 g of polymer (3). Polymer (3) was provided with a functional group having a structure derived from aminothiahexanate. Here, the amount of the basic functional group was 2.5 mmol/g per unit weight of polymer (3).

Thereafter, polymer (3) was dipped into ion exchange water, and allowed to absorb the ion exchange water; thus, a gel, swelled to approximately 3 times per 1 ml of polymer (3), was obtained as a polymer gel (cross-linking polymer gel) in accordance with the present invention (ratio of swell: 3).

Embodiment 4

To a reaction container having a thermometer, a mixer, a titration device and a reflux condenser were loaded 400 g of cyclohexane serving as a solvent and a fixed amount of suspension agent, and stirred. Next, to this reaction container were added 29 g of a monomer component made of N,N-diallylamine and acrylic acid and trimethylolpropanetriacrylate serving as a cross-linking agent, and the mixed solution was heated to 70° C. Here, the above-mentioned N,N-diallylamine was added so that the amount of use of N,N-diallylamine in the monomer component is set at 30 mole %. Further, trimethylolpropanetriacrylate was added so that the amount of use of trimethylolpropanetriacrylate in the reaction solution was set at 1%. Meanwhile, to the titration device was loaded a fixed amount of an aqueous solution of 2,2'-azobis (2-amidinopropane)dihydrochloride (manufactured by Wako Pure Chemical Industries corporation; tradename V-50) having a predetermined concentration as a polymerization initiator. Next, the polymerization initiator inside the titration device was dropped into the above-mentioned mixed solution in 10 minutes. Thereafter, the reaction solution inside the reaction container was further stirred for three hours, and then the stirring was stopped. Thereafter, the reaction solution was subjected to a decantation process, washed by a fixed amount of cyclohexane, and then dried at 80° C. under reduced pressure; thus, polymer (4) weighing approximately 27 g was obtained. Here, the amount of the basic functional group was 3.8 mmol/g per unit weight of polymer (4).

Thereafter, polymer (4) was dipped into ion exchange water, and allowed to absorb the ion exchange water; thus, a gel, swelled to approximately 8 times per 1 ml of polymer (4), was obtained as a polymer gel (cross-linking polymer gel) in accordance with the present invention (ratio of swell: 8).

Embodiment 5

To N,N-diallylamine and N,N,N-triallylamine were respectively added the same amount of hydrochloric acid (aqueous solution of 36% by weight) and neutralized so that an N,N-diallylamine hydrochloride aqueous solution and an N,N,N-triallylamine hydrochloride aqueous solution, each serving as an aqueous solution containing a monomer, were respectively prepared. Next, the N,N-diallylamine hydrochloride aqueous solution and the N,N,N-triallylamine hydrochloride aqueous solution were mixed in a ratio of 1:1 in weight ratio, and then, to this aqueous solution was added 0.8% by weight of 2,2'-azobis-(2-amidinopropane) dihydrochloride serving as a polymerization initiator; thus, a water phase is formed.

Meanwhile, toluene and 1,1,1-trichloroethane, which serve as dispersion medium, are mixed at a volume ratio of 1:1, and then to this mixed solution were respectively added 0.8% by weight of sorbitanmonostearate and polyvinyl alcohol both serving as suspension agents; thus an oil phase was formed.

Next, predetermined amounts of the above-mentioned water phase and oil phase were loaded to a separable flask (reaction container) with a capacity of 1 L provided with a thermometer, a mixer and a reflux condenser so as to be set at a volume ratio of 1:4. Further, the two phases of reaction liquids were gently mixed and stirred with stirring blades that rotate at the number of revolution 200 rpm so as to be polymerized for four hours at 55° C. and then for two hours at 75° C.

Successively, the reaction liquid was cooled off, and polymer beads (solid) thus produced were filtrated and taken out. Thereafter, these polymer beads were dried at 70° C. under reduced pressure, thereby obtaining grainy resin (5) having an average particle diameter of 0.6 mm, which is a grainy resin having a cyclic amine structure. Here, the amount of the basic functional group was 6.5 mmol/g per unit weight of grainy resin (5).

Embodiment 6

The same reactions and operations as embodiment 5 were carried out except that in embodiment 5, the method for preparing the water phase containing a monomer was changed to the following method, thereby producing a grainy resin having a cyclic amine structure. In other words, N,N,N-triallylamine was neutralized by adding hydrochloric acid (aqueous solution of 36% by weight) so that an aqueous solution containing a monomer (N,N,N-triallylamine hydrochloride) was prepared, and then to this aqueous solution was added 0.8% by weight of 2-2'-azobis-(2-amidinopropane)dihydrochloride serving as a polymerization initiator; thus, a water phase was formed.

Meanwhile, toluene and 1,1,1-trichloroethane, which serve as dispersion medium, are mixed at a volume ratio of 1:1, and then to this mixed solution were respectively added 0.8% by weight of sorbitanmonostearate and polyvinyl alcohol both serving as a suspension agent; thus an oil phase was formed.

Next, predetermined amounts of the above-mentioned water phase and oil phase were loaded to a separable flask (reaction container) with a capacity of 1 L provided with a thermometer, a mixer and a reflux condenser so as to be set at a volume ratio of 1:4. Further, the two phases of reaction liquids were gently mixed and stirred with stirring blades that rotate at the number of revolution 200 rpm so as to be polymerized for four hours at 55° C., and then for two hours at 75° C. Thus, a polymer having a cyclic amino structure derived from the above-mentioned monomer was obtained. Successively, the reaction liquid was cooled off, and polymer beads (solid) thus produced were filtrated and taken out. Thereafter, these polymer beads were dried at 70° C. under reduced pressure, thereby obtaining polymer (6) having a cyclic amine structure derived from the monomer. Here, the amount of the basic functional group was 5.8 mmol/g per unit weight of polymer (6).

Embodiment 7

N,N,N-triallylamine was neutralized by adding hydrochloric acid (aqueous solution of 36% by weight) so that an aqueous solution containing a monomer (N,N,N-triallylamine hydrochloride) was prepared, and then to this aqueous solution was added 20% by weight of triethyleneglycoldivinylether serving as a cross-linking agent. Thereafter, to this was further added 0.8% by weight of 2-2'-azobis-(2-amidinopropane)dihydrochloride serving as a polymerization initiator; thus, a water phase was formed.

Meanwhile, toluene and 1,1,1-trichloroethane, which serve as dispersion medium, are mixed at a volume ratio of 1:1, and then to this mixed solution were respectively added 0.8% by weight of sorbitanmonostearate and polyvinyl alcohol both serving as a suspension agent; thus an oil phase was formed.

Next, predetermined amounts of the above-mentioned water phase and oil phase were loaded to a separable flask (reaction container) with a capacity of 1 L provided with a thermometer, a mixer and a reflux condenser so as to be set at a volume ratio of 1:4. Further, the two phases of reaction liquids were gently mixed and stirred with stirring blades that rotate at the number of revolution 200 rpm so as to be polymerized for four hours at 55° C., and then for two hours at 75° C.

Successively, the reaction liquid was cooled off, and polymer beads (solid) thus produced were filtrated and taken out. Thereafter, these polymer beads were dried at 70° C. under reduced pressure, thereby obtaining grainy resin (7) having an average particle diameter of 0.6 mm, which is a grainy resin having a cyclic amine structure as a cross-linking high polymer product. Here, the amount of the basic functional group, which was found from the content of nitrogen per unit weight through element analysis, was 5.8 mmol/g per unit weight of grainy resin (7).

Embodiment 8

The polymer (6)(6 g) obtained in embodiment 6 was impregnated with a mixture of 2.12 g of a methanol solution of 12% by weight of diethyleneglycoldivinylether and 7% by weight of a 2,2'-azobis-(2-amidinopropane) dihydrochloride aqueous solution (polymerization initiator). Next, the polymer (6) impregnated with the mixture was heated for three hours in 100 g of toluene while being subject to nitrogen bubbling. At this time, the temperature of the toluene phase was set at 67° C. After having been cooled, the reactant thus obtained was washed with toluene, and further washed with methanol, and then vacuum-dried at 60° C.; thus, resin (8), obtained by treating the polymer (6) with diethyleneglycoldivinylether, was produced. The amount of the basic functional group was 5.8 mmol/g per unit weight of polymer (8).

Embodiment 9

A hydration reaction of acrolein was carried out as an addition reaction (Michel addition reaction) of a compound containing a hydroxyl group to an $\alpha$, $\beta$-unsaturated compound that uses the polymer gel obtained in embodiment 1 as a catalyst. First, after loading a predetermined amount of water into a reaction container provided with a thermometer, a mixing device, etc., a predetermined amount of acrolein (an active-hydrogen-containing compound) was loaded to the reaction container so that the concentration in the aqueous solution was set at 28% by weight. Next, 19% by volume of the above-mentioned polymer gel was added to the acrolein aqueous solution as a catalyst, thereby forming a reaction solution. Thereafter, the acrolein was hydrated by allowing the reaction solution to react for 5 hours at 90° C. while being stirred.

After completion of the reaction, the reaction solution was filtered, and the filtrate was analyzed by gaschromatograph (GC), with the result that the conversion of acrolein was 57% and that the selectivity of a total of 3-hydroxypropanal and its dimer that were the hydration reaction products was 89%. Here, the conversion of the above-mentioned acrolein (reaction substrate) and the selectivity of the 3-hydroxypropanal (reaction product) and its dimmer (reaction product from a side reaction) are defined in the same manner as described earlier.

Conversion of acrolein (%) =

$$\frac{\text{Number of moles of acrolein consumed}}{\text{Number of moles of acrolein supplied}} \times 100$$

Selectivity of 3-hydroxypropanal (%) =

$$\frac{\text{Number of moles of acrolein converted to 3-hydroxypropanal}}{\text{Number of moles of acrolein consumed}} \times 100$$

Selectivity of 3-hydroxypropanal dimer (%) =

$$\frac{\text{Number of moles of acrolein converted to 3-hydroxypropanal dimer}}{\text{Number of moles of acrolein consumed}} \times 100$$

The above-mentioned results show that the polymer gel obtained in the present embodiment makes it possible to activate the active hydrogen of water, and also to obtain 3-hydroxypropanal and its dimer with high selectivity.

Embodiment 10

A hydroxy propylation reaction of n-butylalcohol was carried out by using polymer (1) obtained in Embodiment 1 as an addition reaction of a heterocyclic compound to an alcohol.

Specifically, n-butyl alcohol (active-hydrogen-containing compound) and propylene oxide were loaded to a reaction container provided with a thermometer, a mixing device, etc. so that the amount of load of propylene oxide to n-butyl alcohol was set at 1.2 times in mole ratio, thereby forming a reaction solution. Next, to the reaction solution was added the aforementioned polymer (1) so that it accounted for 10% by weight to n-butylalcohol. Thereafter, the reaction solution was allowed to react for 4.5 hours at 90° C. while being stirred so that the aforementioned polymer (1) was allowed to swell in the reaction solution; thus, a polymer gel was formed, and the hydroxy propylation reaction of n-butylalcohol was carried out by using the polymer gel as a catalyst.

After completion of the reaction, the reaction solution was filtered, and the filtrate was analyzed by GC. The results showed that the conversion of n-butyl alcohol was 67%, that the selectivity of a propylene oxide 1-mole adduct (reaction product) in which one mole of propyleneoxide was added to n-butyl alcohol was 86%, and that the selectivity of a propylene oxide 2-mole adduct (reaction product from side reactions) in which two moles of propyleneoxide was added to n-butyl alcohol was 14%. Here, the conversion of the above-mentioned n-butyl alcohol (reaction substrate) and the selectivities of the propyleneoxide 1-mole adduct and propyleneoxide 2-mole adduct are defined in the same manner as described earlier.

Embodiment 11

A hydroxy propylation reaction of phenol was carried out by using polymer (1) obtained in Embodiment 1 as an addition reaction of a heterocyclic compound to a phenol.

Specifically, phenol (active-hydrogen-containing compound) and propylene oxide were loaded to a reaction container provided with a thermometer, a mixing device, etc. so that the amount of load of propylene oxide to phenol was set at 1.6 times in mole ratio, thereby forming a reaction solution. Next, to this reaction solution was added the aforementioned polymer (1) so that it accounted for 10% by weight to phenol. Thereafter, the reaction solution was allowed to react for 4.5 hours at 90° C. while being stirred so that the aforementioned polymer (1) was allowed to swell in the reaction solution; thus, a polymer gel was formed, and the hydroxy propylation reaction of phenol was carried out by using the polymer gel as a catalyst.

After completion of the reaction, the reaction solution was filtered, and the filtrate was analyzed by GC. The results showed that the conversion of phenol was 100%, that the selectivity of a propylene oxide 1-mole adduct (reaction product) in which one mole of propyleneoxide was added to phenol was 94%, and that the selectivity of a propylene oxide 2-mole adduct (reaction product from side reactions) in which two moles of propyleneoxide was added to phenol was 5%. Here, the conversion of the above-mentioned phenol (reaction substrate) and the selectivities of the propyleneoxide 1-mole adduct and propyleneoxide 2-mole adduct are defined in the same manner as described earlier.

Embodiment 12

A hydroxy propylation reaction of 2-pyrolidone was carried out by using polymer (1) obtained in Embodiment 1 as an addition reaction of a heterocyclic compound to an amide.

Specifically, 2-pyrolidone (active-hydrogen-containing compound) and propylene oxide were loaded to a reaction container provided with a thermometer, a mixing device, etc. so that the amount of load of propylene oxide to 2-pyrolidone was set at 1.4 times in mole ratio, thereby forming a reaction solution. Next, to this reaction solution was added the aforementioned polymer (1) so that it accounted for 10% by weight to 2-pyrolidone. Thereafter, the reaction solution was allowed to react for 5 hours at 90° C. while being stirred so that the aforementioned polymer (1) was allowed to swell in the reaction solution; thus, a polymer gel was formed, and the hydroxy propylation reaction of 2-pyrolidone was carried out by using the polymer gel as a catalyst.

After completion of the reaction, the reaction solution was filtered, and the filtrate was analyzed by GC. The results showed that the conversion of 2-pyrolidone was 44%, that the selectivity of a propylene oxide 1-mole adduct (reaction product) in which one mole of propyleneoxide was added to 2-pyrolidone was 94%, and that the selectivity of a propylene oxide 2-mole adduct (reaction product from side reactions) in which two moles of propyleneoxide was added to 2-pyrolidone was 2%. Here, the conversion of the above-mentioned 2-pyrolidone (reaction substrate) and the selectivities of the propyleneoxide 1-mole adduct and propyleneoxide 2-mole adduct are defined in the same manner as described earlier.

Embodiment 13

By using polymer (1) obtained in Embodiment 1, a condensation reaction (Knoevenagel condensation reaction) of malonic acid and benzaldehyde, which is a reaction relating to a hydrogen atom (α-hydrogen atom) bonding to a carbon atom adjacent to an electron attractive group, was carried out.

Specifically, malonic acid (active-hydrogen-containing compound) and benzaldehyde were loaded to a reaction container provided with a thermometer, a mixing device, etc. so that the mole ratio of the two components was set at 1:1, thereby forming a reaction solution. Next, to this reaction solution was added the aforementioned polymer (1) so that it accounted for 10% by weight to malonic acid. Thereafter, the reaction solution was allowed to react for 11 hours at 90° C. while being stirred so that the aforementioned polymer (1) was allowed to swell in the reaction solution; thus, a polymer gel was formed, and the condensation reaction of malonic acid and benzaldehyde was carried out by using the polymer gel as a catalyst.

After completion of the reaction, the reaction solution was filtered, and the filtrate was analyzed by GC. The results showed that the conversion of malonic acid was 61% and that the selectivity of cinnamic acid (reaction product) was 84%. Here, the conversion of the malonic acid (reaction substrate) and the selectivity of the cinnamic acid are defined in the same manner as described earlier.

Embodiment 14

A hydroxy propylation reaction of 2-pyrolidone was carried out as an addition reaction of a cyclic hetero compound to an amide by using the polymer gel obtained in Embodiment 2 as a catalyst. First, 2-pyrolidone (active-hydrogen-containing compound) and propylene oxide were loaded to a reaction container provided with a thermometer, a mixing device, etc. so that the amount of load of propylene oxide to 2-pyrolidone was set at 1.4 times in mole ratio, thereby forming a reaction solution. Next, to this reaction solution was added the above-mentioned polymer gel as a catalyst so that it accounted for 10% by weight to 2-pyrolidone. Thereafter, the reaction solution was allowed to react for 5 hours at 90° C. while being stirred so that the hydroxy propylation reaction of 2-pyrolidone was carried out.

After completion of the reaction, the reaction solution was filtered, and the filtrate was analyzed by GC. The results showed that the conversion of 2-pyrolidone was 44%, that the selectivity of a propylene oxide 1-mole adduct (reaction product) in which one mole of propyleneoxide was added to 2-pyrolidone was 94%, and that the selectivity of a propylene oxide 2-mole adduct (reaction product from side reactions) in which two moles of propyleneoxide was added to 2-pyrolidone was 2%. Here, the conversion of the above-mentioned 2-pyrolidone (reaction substrate) and the selectivities of the propyleneoxide 1-mole adduct and propyleneoxide 2-mole adduct are defined in the same manner as described earlier.

As a result, it is found that the polymer gel used in the present embodiment makes it possible to activate the active hydrogen in 2-pyrolidone and also to provide a propylene oxide 1-mole adduct to 2-pyrolidone with high selectivity.

Embodiment 15

A hydroxy propylation reaction of acrylic acid was carried out as an addition reaction of a cyclic hetero compound to a carboxylic acid by using the polymer gel obtained in Embodiment 2 as a catalyst. First, acrylic acid (active-hydrogen-containing compound) and propylene oxide were loaded to a reaction container provided with a thermometer, a mixing device, etc. so that the amount of load of propylene oxide to acrylic acid was set at 1.2 times in mole ratio, thereby forming a reaction solution. Next, to this reaction solution was added the above-mentioned polymer gel as a catalyst so that it accounted for 10% by weight to acrylic acid. Thereafter, the reaction solution was allowed to react for 2 hours at 90° C. while being stirred so that the hydroxy propylation reaction of acrylic acid was carried out.

After completion of the reaction, the reaction solution was filtered, and the filtrate was analyzed by GC. The results showed that the conversion of acrylic acid was 95%, that the selectivity of a propylene oxide 1-mole adduct (reaction product) in which one mole of propyleneoxide was added to acrylic acid was 92%, and that the selectivity of a propylene oxide 2-mole adduct (reaction product from side reactions) in which two moles of propyleneoxide was added to acrylic acid was 8%. Here, the conversion of the above-mentioned acrylic acid (reaction substrate) and the selectivities of the propyleneoxide 1-mole adduct and propyleneoxide 2-mole adduct are defined in the same manner as described earlier.

As a result, it is found that the polymer gel used in the present embodiment makes it possible to activate the active hydrogen in acrylic acid and also to provide a propylene oxide 1-mole adduct to acrylic acid with high selectivity.

Embodiment 16

A hydroxy propylation reaction of phenol was carried out by using the polymer gel obtained in Embodiment 2 as an addition reaction of a cyclic hetero compound to a phenol. First, phenol (active-hydrogen-containing compound) and propylene oxide were loaded to a reaction container provided with a thermometer, a mixing device, etc. so that the amount of load of propylene oxide to phenol was set at 1.6 times in mole ratio, thereby forming a reaction solution. Next, to this reaction solution was added the above-mentioned polymer gel as a catalyst so that it accounted for 10% by weight to phenol. Thereafter, the reaction solution was allowed to react for 4.5 hours at 90° C. while being stirred so that the hydroxy propylation reaction of phenol was carried out.

After completion of the reaction, the reaction solution was filtered, and the filtrate was analyzed by GC. The results showed that the conversion of phenol was 100%, that the selectivity of a propylene oxide 1-mole adduct (reaction product) in which one mole of propyleneoxide was added to phenol was 94%, and that the selectivity of a propylene oxide 2-mole adduct (reaction product from side reactions) in which two moles of propyleneoxide was added to phenol was 5%. Here, the conversion of the above-mentioned phenol (reaction substrate) and the selectivities of the propyleneoxide 1-mole adduct and propyleneoxide 2-mole adduct are defined in the same manner as described earlier.

As a result, it is found that the polymer gel used in the present embodiment makes it possible to activate the active hydrogen in phenol and also to provide a propylene oxide 1-mole adduct to phenol with high selectivity.

Embodiment 17

A hydroxy propylation reaction of hydroquinone was carried out by using the polymer gel obtained in Embodiment 2 as an addition reaction of a cyclic hetero compound to a phenol. First, hydroquinone (active-hydrogen-containing compound) and propylene oxide were loaded to a reaction container provided with a thermometer, a mixing device, etc. so that the amount of load of propylene oxide to phenol was set at 2.0 times in mole ratio, thereby forming a reaction solution. Next, to this reaction solution was added the above-mentioned polymer gel as a catalyst so that it accounted for 26% by weight to hydroquinone. Thereafter, the reaction solution was allowed to react for 6.5 hours at 90° C. while being stirred so that the hydroxy propylation reaction of hydroquinone was carried out.

After completion of the reaction, the reaction solution was filtered, and the filtrate was analyzed by GC. The results showed that the conversion of hydroquinone was 84%, and that the selectivity of a propylene oxide 2-mole adduct (reaction product from side reactions) in which two moles of propyleneoxide was added to hydroquinone was 100%. Here, the conversion of the above-mentioned hydroquinone (reaction substrate) and the selectivity of propyleneoxide 2-mole adduct are defined in the same manner as described earlier.

As a result, it is found that the polymer gel used in the present embodiment makes it possible to activate the active hydrogen in hydroquinone and also to provide a propylene oxide 2-mole adduct to hydroquinone with high selectivity.

Embodiment 18

A hydroxy ethylation reaction of acrylic acid was carried out as an addition reaction of a cyclic hetero compound to a carboxylic acid by using the polymer gel obtained in Embodiment 2 as a catalyst. First, 20 g of acrylic acid (active-hydrogen-containing compound) was loaded to a reaction container provided with a thermometer, a gas supplying tube, a mixing device, etc., and to this was added the above-mentioned polymer gel as a catalyst so that it accounted for 10% by weight to acrylic acid. After the acrylic acid had been heated to 70° C. while being stirred, ethylene oxide was continuously introduced into the reaction container through the gas supplying tube in four hours so that the amount of load of ethylene oxide to acrylic acid was set at 1.1 times in mole ratio. Then, the reaction solution was further matured for three hours at 70° C. while being stirred; thus, the hydroxy ethylation reaction of acrylic acid was carried out.

After completion of the reaction, the reaction solution was filtered, and the filtrate was analyzed by GC. The results showed that the conversion of acrylic acid was 90%, that the selectivity of an ethylene oxide 1-mole adduct (reaction product) in which one mole of ethyleneoxide was added to acrylic acid was 91%, and that the selectivity of an ethylene oxide 2-mole adduct (reaction product from side reactions) in which two moles of ethylene oxide was added to acrylic acid was 7%. Here, the conversion of the above-mentioned acrylic acid (reaction substrate) and the selectivities of the ethyleneoxide 1-mole adduct and ethyleneoxide 2-mole adduct are defined in the same manner as described earlier.

As a result, it is found that the polymer gel used in the present embodiment makes it possible to activate the active hydrogen in acrylic acid and also to provide an ethylene oxide 1-mole adduct to acrylic acid with high selectivity.

Embodiment 19

By using the polymer gel obtained in Embodiment 3 as a catalyst, a condensation reaction (Knoevenagel condensation reaction) of malonic acid and benzaldehyde, which is a reaction relating to a hydrogen atom (α-hydrogen atom) bonding to a carbon atom adjacent to an electron attractive group, was carried out. First, malonic acid (active-hydrogen-containing compound) and benzaldehyde were loaded to a reaction container provided with a thermometer, a mixing device, etc. so that the amount of load of benzaldehyde to malonic acid was set at 1.0 in mole ratio, thereby forming a reaction solution. Next, to this reaction solution was added the above-mentioned gel as a catalyst so that it accounted for 0.8 times in weight ratio to malonic acid. Thereafter, the reaction solution was allowed to react for 11 hours at 90° C. while being stirred; thus, the condensation reaction of malonic acid and benzaldehyde was carried out.

After completion of the reaction, the reaction solution was filtered, and the filtrate was analyzed by GC. The results showed that the conversion of benzaldehyde was 61% and that the selectivity of cinnamic acid (reaction product) was 84%. In other words, the yield of cinnamic acid was 51% in the present embodiment. Here, the conversion of the benzaldehyde (reaction substrate) and the selectivity of the cinnamic acid are defined in the same manner as described earlier.

As a result, it is found that the polymer gel obtained in the present embodiment makes it possible to activate the active hydrogen of malonic acid which is a compound that contains an active hydrogen, that is, a hydrogen atom (α-hydrogen atom) bonding to a carbon atom adjacent to an electron attractive group, and also to provide cinnamic acid with high selectivity.

Embodiment 20

By using the polymer gel obtained in Embodiment 4 as a catalyst, a condensation reaction (Knoevenagel condensation reaction) of malonic acid and p-methoxybenzaldehyde, which is a reaction relating to a hydrogen atom (α-hydrogen atom) bonding to a carbon atom adjacent to an electron attractive group, was carried out. First, malonic acid (active-hydrogen-containing compound) and p-methoxybenzaldehyde were loaded to a reaction container provided with a thermometer, a mixing device, etc. so that the amount of load of methoxybenzaldehyde to malonic acid was set at 0.5 in mole ratio, thereby forming a reaction solution. Next, to this reaction solution was added the above-mentioned gel as a catalyst so that it accounted for 1.0 time in weight ratio to malonic acid. Thereafter, the reaction solution was allowed to react for 6 hours at 90° C. while being stirred; thus, the condensation reaction of malonic acid and p-methoxybenzaldehyde was carried out.

After completion of the reaction, the reaction solution was filtered, and the filtrate was analyzed by GC. The results showed that the conversion of p-methoxybenzaldehyde was 53%. Here, the conversion of the p-methoxybenzaldehyde (reaction substrate) is defined in the same manner as described earlier.

As a result, it is found that the polymer gel obtained in the present embodiment makes it possible to activate the active hydrogen of malonic acid which is a compound containing an active hydrogen, that is, a hydrogen atom (α-hydrogen atom) bonding to a carbon atom adjacent to an electron attractive group, and also to provide p-methoxybenzaldehyde with high selectivity.

Embodiment 21

By using the polymer gel obtained in Embodiment 4 as a catalyst, a condensation reaction (Knoevenagel condensation reaction) of malonic acid and p-hydroxybenzaldehyde was carried out through the same reaction and operation as those in embodiment 20 except that p-hydroxybenzaldehyde was used instead of p-methoxybenzaldehyde.

After completion of the reaction, the reaction solution was filtered, and the filtrate was analyzed by GC. The results showed that the conversion of p-hydroxybenzaldehyde was 53%. Here, the conversion of the p-hydroxybenzaldehyde (reaction substrate) is defined in the same manner as described earlier.

As a result, it is found that the polymer gel obtained in the present embodiment makes it possible to activate the active hydrogen of malonic acid which is a compound that contains an active hydrogen, that is, a hydrogen atom (α-hydrogen atom) bonding to a carbon atom adjacent to an electron attractive group, and also to provide p-hydroxybenzaldehyde with high selectivity.

Embodiment 22

By using the polymer gel obtained in Embodiment 4 as a catalyst, a condensation reaction (Knoevenagel condensation reaction) of malonic acid and p-methylbenzaldehyde was carried out through the same reaction and operation as those in embodiment 20 except that p-methylbenzaldehyde was used instead of p-methoxybenzaldehyde.

After completion of the reaction, the reaction solution was filtered, and the filtrate was analyzed by GC. The results showed that the conversion of p-methylbenzaldehyde was 64%. Here, the conversion of the p-methylbenzaldehyde (reaction substrate) is defined in the same manner as described earlier.

As a result, it is found that the polymer gel obtained in the present embodiment makes it possible to activate the active hydrogen of malonic acid which is a compound that contains an active hydrogen, that is, a hydrogen atom (α-hydrogen atom) bonding to a carbon atom adjacent to an electron attractive group, and also to provide p-methylbenzaldehyde with high selectivity.

Embodiment 23

By using the polymer gel obtained in Embodiment 4 as a catalyst, a condensation reaction (Knoevenagel condensation reaction) of malonic acid and p-chlorobenzaldehyde was carried out through the same reaction and operation as those in embodiment 20 except that p-chlorobenzaldehyde was used instead of p-methoxybenzaldehyde.

After completion of the reaction, the reaction solution was filtered, and the filtrate was analyzed by GC. The results showed that the conversion of p-chlorobenzaldehyde was 71%. Here, the conversion of the p-chlorobenzaldehyde (reaction substrate) is defined in the same manner as described earlier.

As a result, it is found that the polymer gel obtained in the present embodiment makes it possible to activate the active hydrogen of malonic acid which is a compound containing an active hydrogen, that is, a hydrogen atom (α-hydrogen atom) bonding to a carbon atom adjacent to an electron attractive group, and also to provide p-chlorobenzaldehyde with high selectivity.

Embodiment 24

By using the polymer gel obtained in Embodiment 4 as a catalyst, a condensation reaction (Knoevenagel condensation reaction) of malonic acid and p-bromobenzaldehyde was carried out through the same reaction and operation as those in embodiment 20 except that p-bromobenzaldehyde was used instead of p-methoxybenzaldehyde.

After completion of the reaction, the reaction solution was filtered, and the filtrate was analyzed by GC. The results showed that the conversion of p-bromobenzaldehyde was 72%. Here, the conversion of the p-bromobenzaldehyde (reaction substrate) is defined in the same manner as described earlier.

As a result, it is found that the polymer gel obtained in the present embodiment makes it possible to activate the active hydrogen of malonic acid which is a compound that contains an active hydrogen, that is, a hydrogen atom (α-hydrogen atom) bonding to a carbon atom adjacent to an electron attractive group, and also to provide p-bromobenzaldehyde with high selectivity.

Embodiment 25

By using the polymer gel obtained in Embodiment 4 as a catalyst, a condensation reaction (Knoevenagel condensation reaction) of ethylcyanoacetate and benzaldehyde, which is a reaction relating to a hydrogen atom (α-hydrogen atom) bonding to a carbon atom adjacent to an electron attractive group, was carried out. First, ethylcyanoacetate (active-hydrogen-containing compound) and benzaldehyde were loaded to a reaction container provided with a thermometer, a mixing device, etc. so that the amount of load of benzaldehyde to ethylcyanoacetate was set at 0.5 times in mole ratio, thereby forming a reaction solution. Next, to this reaction solution was added the above-mentioned polymer gel as a catalyst so that it accounted for 0.8 times in weight ratio to ethylcyanoacetate. Thereafter, the reaction solution was allowed to react for 18 hours at 90° C. while being stirred; thus, the condensation reaction of ethylcyanoacetate and benzaldehyde was carried out.

After completion of the reaction, the reaction solution was filtered, and the filtrate was analyzed by GC. The results showed that the conversion of benzaldehyde was 96%, and as a result of an analysis by mass chromatography, it was found that the reaction product was a corresponding α-cyanoesteracrylate. Here, the conversion of the benzaldehyde (reaction substrate) is defined in the same manner as described earlier.

As a result, it is found that the polymer gel obtained in the present embodiment makes it possible to activate the active hydrogen of ethylcyanoacetate which is a compound that contains an active hydrogen, that is, a hydrogen atom (α-hydrogen atom) bonding to a carbon atom adjacent to an electron attractive group, and also to provide benzaldehyde with high selectivity.

Embodiment 26

By using the polymer gel obtained in Embodiment 4 as a catalyst, a condensation reaction (Knoevenagel condensation reaction) of ethylcyanoacetate and methylethylketone, which is a reaction relating to a hydrogen atom (α-hydrogen atom) bonding to a carbon atom adjacent to an electron attractive group, was carried out. First, ethylcyanoacetate (active-hydrogen-containing compound) and methylethylketone were loaded to a reaction container provided with a thermometer, a mixing device, etc. so that the amount of load of methylethylketone to ethylcyanoacetate was set at 1.0 time in mole ratio, thereby forming a reaction solution. Next, to this reaction solution was added the above-mentioned polymer gel as a catalyst so that it accounted for 0.09 times in weight ratio to ethylcyanoacetate. Thereafter, the reaction solution was allowed to react for 18 hours at 90° C. while being stirred; thus, the condensation reaction of ethylcyanoacetate and methylethylketone was carried out.

After completion of the reaction, the reaction solution was filtered, and the filtrate was analyzed by GC. The results showed that the conversion of ethylcyanoacetate was 96%, and as a result of an analysis by mass chromatography, it was found that the reaction product was a corresponding α-cyanoacrylate. Here, the conversion of the ethylcyanoacetate (reaction substrate) is defined in the same manner as described earlier.

As a result, it is found that the polymer gel obtained in the present embodiment makes it possible to activate the active hydrogen of ethylcyanoacetate which is a compound that contains active hydrogen, that is, a hydrogen atom (α-hydrogen atom) bonding to a carbon atom adjacent to an electron attractive group, and also to provide ethylcyanoacetate with high selectivity.

Embodiment 27

By using the polymer gel obtained in Embodiment 4 as a catalyst, a condensation reaction (Knoevenagel condensation reaction) of ethylcyanoacetate and propionaldehyde, which is a reaction relating to a hydrogen atom (α-hydrogen atom) bonding to a carbon atom adjacent to an electron attractive group, was carried out. First, ethylcyanoacetate (active-hydrogen-containing compound) and propionaldehyde were loaded to a reaction container provided with a thermometer, a mixing device, etc. so that the amount of load of propionaldehyde to ethylcyanoacetate was set at 1.0 time in mole ratio, thereby forming a reaction solution. Next, to this reaction solution was added the above-mentioned polymer gel as a catalyst so that it accounted for 0.09 times in weight ratio to ethylcyanoacetate. Thereafter, the reaction solution was allowed to react for 6 hours at 90° C. while being stirred; thus, the condensation reaction of ethylcyanoacetate and propionaldehyde was carried out.

After completion of the reaction, the reaction solution was filtered, and the filtrate was analyzed by GC. The results showed that the conversion of ethylcyanoacetate was 82%, and as a result of an analysis by mass chromatography, it was found that the reaction product was a corresponding α-cyanoesteracrylate. Here, the conversion of the ethylcyanoacetate (reaction substrate) is defined in the same manner as described earlier.

As a result, it is found that the polymer gel obtained in the present embodiment makes it possible to activate the active hydrogen of ethylcyanoacetate which is a active-hydrogen-containing compound, that is, a hydrogen atom (α-hydrogen atom) bonding to a carbon atom adjacent to an electron attractive group, and also to provide ethylcyanoacetate with high selectivity.

Embodiment 28

A hydroxy ethylation reaction of acrylic acid was carried out as an addition reaction of a cyclic hetero compound to a carboxylic acid by using the grainy resin (5) obtained in Embodiment 5. First, 20 g of acrylic acid (active-hydrogen-containing compound) and 1 g of the above-mentioned grainy resin (5) were loaded to a reaction container provided with a thermometer, a gas-supplying tube, a mixing device, etc. After the acrylic acid had been heated to 70° C. while being stirred, 15 g of ethylene oxide was continuously introduced into the reaction container through the gas supplying tube in 2.5 hours. Then, the reaction solution was further matured for two hours at 70° C. while being stirred so that the above-mentioned grainy resin (5) was allowed to swell in the reaction solution and produce a polymer gel; thus, the hydroxy ethylation reaction of acrylic acid was carried out by using this polymer gel as a catalyst.

After completion of the reaction, the reaction solution was filtered, and the filtrate was analyzed by GC. The results showed that the conversion of acrylic acid was 78.8%, that the selectivity of an ethylene oxide 1-mole adduct (reaction product) in which one mole of ethyleneoxide was added to acrylic acid was 93.7%, that the selectivity of an ethylene oxide 2-mole adduct (reaction product from side reactions) in which two moles of ethylene oxide was added to acrylic acid was 6.1%, and that the selectivity of diester (reaction product from side reactions) obtained through esterification of acrylic acid by hydroxyethylacrylate was 0.17%. Here, the conversion of the above-mentioned acrylic acid (reaction substrate) and the selectivities of the ethyleneoxide 1-mole adduct, ethyleneoxide 2-mole adduct and diester obtained through esterification of acrylic acid by hydroxyethylacrylate are defined in the same manner as described earlier. Moreover, the apparent specific gravity of the polymer gel (catalyst) in the reaction solution was 0.075 g/cc, and the amount of basic active sites (that is, active groups derived from N,N-diallylamine and N,N,N-triallylamine) of the above-mentioned polymer gel per unit volume in the reaction solution was 0.488 mmol/cc.

Embodiment 29

A hydroxy propylation reaction of acrylic acid was carried out as an addition reaction of a cyclic hetero compound to a carboxylic acid by using the grainy resin (5) obtained in Embodiment 5. Specifically, acrylic acid (active-hydrogen-containing compound) and propyleneoxide were loaded to a reaction container provided with a thermometer, a mixing device, etc. so that the amount of load of propyleneoxide to acrylic acid was set at 1.2 times in mole ratio, thereby forming a reaction solution. Next, to this reaction solution was added 10%. by weight of the above-mentioned grainy resin (5) with respect to the acrylic acid. Then, the reaction solution was allowed to react for two hours at 90° C. while being stirred so that the above-mentioned grainy resin (5) was allowed to swell in the reaction solution and produce a polymer gel; thus, the hydroxy propylation reaction of acrylic acid was carried out by using this polymer gel as a catalyst.

After completion of the reaction, the reaction solution was filtered, and the filtrate was analyzed by GC. The results showed that the conversion of acrylic acid was 96%, that the selectivity of a propylene oxide 1-mole adduct (reaction product) in which one mole of propylene oxide was added to acrylic acid was 94%, and that the selectivity of a propylene oxide 2-mole adduct (reaction product from side reactions) in which two moles of propylene oxide was added to acrylic acid was 5%. Here, the conversion of the above-mentioned acrylic acid (reaction substrate) and the selectivities of the propyleneoxide 1-mole adduct and propyleneoxide 2-mole adduct to acrylic acid are defined in the same manner as described earlier.

As a result, it is found that the polymer gel made from the grainy resin (5) obtained in Embodiment 5 reacts as a catalyst for a hydroxypropylation reaction of acrylic acid, which is an addition reaction of a cyclic hetero compound to a carboxylic acid (unsaturated carboxylic acid).

Embodiment 30

A hydroxyethylation reaction of acrylic acid was carried out by using the polymer gel that had been formed by allowing the polymer (6) obtained in Embodiment 6 to swell in the reaction solutwn as a catalyst through the same reactions and operations as those of Embodiment 28 except that the polymer (6) obtained in Embodiment 6 was used instead of the grainy resin (5) obtained in Embodiment 5.

The results showed that the conversion of acrylic acid was 88.6%, that the selectivity of an ethylene oxide 1-mole adduct (reaction product) in which one mole of ethylene oxide was added to acrylic acid was 94.1%, that the selectivity of an ethylene oxide 2-mole adduct (reaction product from side reactions) in which two moles of ethylene oxide was added to acrylic acid was 5.8%, and that the selectivity of diester (reaction product from side reactions) made through the ethylation of acrylic acid by hydroxyethylacrylate was 0.11%. Here, the conversion of the above-mentioned acrylic acid (reaction substrate) and the selectivities of the ethyleneoxide 1-mole adduct, ethyleneoxide 2-mole adduct and diester made through the ethylation of acrylic acid by hydroxyethylacrylate are defined in the same manner as described earlier. Moreover, the apparent specific gravity of the polymer gel (catalyst) in the reaction solution was 0.075 g/cc, and the amount of basic active sites (that is, active groups derived from N,N,N-triallylamine) of the above-mentioned polymer gel per unit volume in the reaction solution was 0.435 mmol/cc.

Embodiment 31

A hydroxyethylation reaction of acrylic acid was carried out by using the polymer gel that had been formed by allowing the grainy resin (7) obtained in Embodiment 7 to swell in the reaction solution as a catalyst through the same reactions and operations as those of Embodiment 28 except that the grainy resin (7) obtained in Embodiment 7 was used instead of the grainy resin (5) obtained in Embodiment 5.

The results showed that the conversion of acrylic acid was 91.6%, that the selectivity of an ethylene oxide 1-mole adduct (reaction product) in which one mole of ethylene oxide was added to acrylic acid was 95.5%, that the selectivity of an ethylene oxide 2-mole adduct (reaction product from side reactions) in which two moles of ethylene oxide was added to acrylic acid was 4.4%, and that the selectivity of diester (reaction product from side reactions) made through the ethylation of acrylic acid by hydroxyethylacrylate was 0.08%. Here, the conversion of the above-mentioned acrylic acid (reaction substrate) and the selectivities of the ethyleneoxide 1-mole adduct, ethyleneoxide 2-mole adduct and diester made through the ethylation of acrylic acid by hydroxyethylacrylate are defined in the same manner as described earlier. Moreover, the apparent specific gravity of the polymer gel (catalyst) in the reaction solution was 0.113 g/cc, and the amount of basic active sites (that is, active groups derived from N,N,N-triallylamine) of the above-mentioned polymer gel per unit volume in the reaction solution was 0.655 mmol/cc.

Embodiment 32

A hydroxyethylation reaction of acrylic acid was carried out by using the polymer gel that had been formed by allowing the grainy resin (7) obtained in Embodiment 7 to swell in the reaction solution as a catalyst through the same reactions and operations as those of Embodiment 31 except that the supplying time of ethylene oxide was changed from 2.5 hours to 4 hours and that the maturing time of the reaction solution after the supply of ethylene oxide was changed from 2 hours to 3 hours in Embodiment 31.

The results showed that the conversion of acrylic acid was 96.1%, that the selectivity of an ethylene oxide 1-mole adduct (reaction product) in which one mole of ethylene oxide was added to acrylic acid was 95.5%, that the selectivity of an ethylene oxide 2-mole adduct (reaction product from side reactions) in which two moles of ethylene oxide was added to acrylic acid was 4.2% and that the selectivity of diester (reaction product from side reactions) made through the ethylation of acrylic acid by hydroxyethylacrylate was 0.21%. Here, the conversion of the above-mentioned acrylic acid (reaction substrate) and the selectivities of the ethyleneoxide 1-mole adduct, ethyleneoxide 2-mole adduct and diester made through the ethylation of acrylic acid by hydroxyethylacrylate are defined in the same manner as described earlier. Moreover, the apparent specific gravity of the polymer gel (catalyst) in the reaction solution was 0.113 g/cc, and the amount of basic active point (that is, active groups derived from N,N,N-triallylamine) of the above-mentioned polymer gel per unit volume in the reaction solution was 0.655 mmol/cc.

Embodiment 33

A hydroxypropylation reaction of acrylic acid was carried out by using the polymer gel that had been formed by allowing the grainy resin (7) obtained in Embodiment 7 to swell in the reaction solution as a catalyst through the same reactions and operations as those of Embodiment 29 except that the grainy resin (7) obtained in Embodiment 7 was used instead of the grainy resin (5) obtained in Embodiment 5.

The results showed that the conversion of acrylic acid was 98%, that the selectivity of a propylene oxide 1-mole adduct (reaction product) in which one mole of propylene oxide was added to acrylic acid was 94%, and that the selectivity of a propylene oxide 2-mole adduct (reaction product from side reactions) in which two moles of propylene oxide was added to acrylic acid was 5%. Here, the conversion of the above-mentioned acrylic acid (reaction substrate) and the selectivities of the propyleneoxide 1-mole adduct and propyleneoxide 2-mole adduct are defined in the same manner as described earlier.

As a result, it is found that the polymer gel made from the grainy resin (7) obtained in Embodiment 7 reacts as a catalyst for a hydroxypropylation reaction of acrylic acid, which is an addition reaction of a cyclic hetero compound to a carboxylic acid (unsaturated carboxylic acid). Moreover, the apparent specific gravity of the polymer gel (catalyst) in the reaction solution was 0.113 g/cc, and the amount of basic active sites (that is, active groups derived from N,N,N-triallylamine) of the above-mentioned polymer gel per unit volume in the reaction solution was 0.655 mmol/cc.

Embodiment 34

A hydroxypropylation reaction of acrylic acid was carried out by using the polymer gel that had been formed by allowing the grainy resin (7) obtained in Embodiment 7 to swell in the reaction solution as a catalyst through the same reactions and operations as those of Embodiment 33 except that the reaction temperature was changed from 90° C. to 70° C. and that the reaction time was changed from 2 hours to 4 hours.

The results showed that the conversion of acrylic acid was 76%, that the selectivity of a propylene oxide 1-mole adduct (reaction product) in which one mole of propylene oxide was added to acrylic acid was 89% and that the selectivity of a propylene oxide 2-mole adduct (reaction product from side reactions) in which two moles of propylene oxide was added to acrylic acid was 9%. Here, the conversion of the above-mentioned acrylic acid (reaction substrate) and the selectivities of the propyleneoxide 1-mole adduct and propyleneoxide 2-mole adduct are defined in the same manner as described earlier. Moreover, the apparent specific gravity of the polymer gel (catalyst) in the reaction solution was 0.113 g/cc, and the amount of basic active point (that is, active groups derived from N,N,N-triallylamine) of the above-mentioned polymer gel per unit volume in the reaction solution was 0.655 mmol/cc.

Embodiment 35

The same reactions and operations as those of Embodiment 34 were carried out except that the resin (8) obtained in Embodiment 8 was used instead of the grainy resin (7) obtained in Embodiment 7. With respect to the hydroxypropylation reaction of acrylic acid using the polymer gel that had been formed by allowing the grainy resin (8) obtained in Embodiment 8 to swell in the reaction solution, the apparent specific gravity of the polymer gel (catalyst) in the reaction solution was 0.13 g/cc, and the amount of basic active point (that is, active groups derived from N,N,N-triallylamine) of the above-mentioned polymer gel per unit volume in the reaction solution was 0.75 mmol/cc.

COMPARATIVE EXAMPLE 1

A hydroxypropylation reaction of pyrolidone was carried out by using the same reactions and operations as those of Embodiment 14 except that, instead of the polymer gel in Embodiment 14, a commercial ion exchange resin "Amberlite IRA-410" (manufactured by Rohm & Haas Co.), which is represented by the following formula, was adopted as a catalyst for comparison:

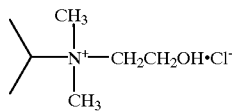

(A)

However, in the above-mentioned reaction, side reactions took place predominantly, with the result that the target product, that is, an adduct in which one mole of propylene oxide is added to pyrolidone, was hardly obtained.

COMPARATIVE EXAMPLE 2

A hydroxypropylation reaction of acrylic acid was carried out by using the same reactions and operations as those of Embodiment 15 except that, instead of the polymer gel in Embodiment 15, dimethylallylamine was adopted as a catalyst for comparison.

The results showed that the conversion of acrylic acid was 76%, that the selectivity of a propylene oxide 1-mole adduct (reaction product) in which one mole of propylene oxide was added to acrylic acid was 87%, and that the selectivity of a propylene oxide 2-mole adduct (reaction product from side reactions) in which two moles of propylene oxide was added to acrylic acid was 13.6%. Moreover, the selectivity of diester (reaction product from side reactions) made through the esterification of acrylic acid by hydroxypropylacrylate was 0.10%. Here, the conversion of the above-mentioned acrylic acid (reaction substrate) and the selectivities of the propyleneoxide 1-mole adduct, propyleneoxide 2-mole adduct and diester made through the esterification of acrylic acid by hydroxypropylacrylate are defined in the same manner as described earlier.

It is found from the results as described above that the application of dimethylallylamine as a catalyst reduces the conversion of acrylic acid.

COMPARATIVE EXAMPLE 3

A hydroxypropylation reaction of acrylic acid was carried out by using the same reactions and operations as those of Embodiment 15 except that, instead of the polymer gel in Embodiment 15, N,N,N-triallylamine was adopted as a catalyst for comparison.

The results showed that the conversion of acrylic acid was 75%, that the selectivity of a propylene oxide 1-mole adduct (reaction product) in which one mole of propylene oxide was added to acrylic acid was 83%, and that the selectivity of a propylene oxide 2-mole adduct (reaction product from side reactions) in which two moles of propylene oxide was added to acrylic acid was 15.4%. Moreover, the selectivity of a compound (reaction product from side reactions) made through the esterification of acrylic acid by propyl alcohol was 0.10%. Here, the conversion of the above-mentioned acrylic acid (reaction substrate) and the selectivities of the propyleneoxide 1-mole adduct, propyleneoxide 2-mole adduct and compound made through the esterification of acrylic acid by propyl alcohol are defined in the same manner as described earlier.

It is found from the results as described above that the application of N,N,N-triallylamine as a catalyst reduces the conversion of acrylic acid.

COMPARATIVE EXAMPLE 4

A condensation reaction of malonic acid and benzaldehyde was carried out by using the same reactions and operations as those of Embodiment 19 except that the polymer gel in Embodiment 19 was not used. In other words, in the present comparative example, a condensation reaction (Knoevenagel condensation reaction) of malonic acid and benzaldehyde was carried out without using a catalyst.

The results showed that the conversion of benzaldehyde was 15%, and that the selectivity of cinnamic acid (reaction product) was 33%. In other words, the yield of cinnamic acid was 5% in the present comparative example. Here, the conversion of the above-mentioned benzaldehyde (reaction substrate) and the selectivity of cinnamic acid are defined in the same manner as described earlier. It is found from the results as described above that no application of a catalyst causes a reduction in the yield of cinnamic acid.

COMPARATIVE EXAMPLE 5

A condensation reaction of malonic acid and benzaldehyde (Knoevenagel condensation reaction) was carried out by using the same reactions and operations as those of Embodiment 19 except that, instead of the polymer gel in Embodiment 19, pyridine was added to malonic acid as a catalyst used for comparison so as to be set 15 times greater than malonic acid in mole ratio and that the reaction time was changed from 11 hours to 8 hours.

The results showed that the conversion of benzaldehyde was 14%, and that the selectivity of cinnamic acid (reaction product) was 57%. In other words, the yield of cinnamic acid was 8% in the present comparative example. Here, the conversion of the above-mentioned benzaldehyde (reaction substrate) and the selectivity of cinnamic acid are defined in the same manner as described earlier. It is found from the results as described above that the application of pyridine as a catalyst requires a large amount of catalyst and results in a low yield in cinnamic acid.

Embodiment 36

In hydration reactions of acrolein in which the polymer gel obtained in Embodiment 1 and the following comparative-use catalysts were used, respective reaction rates were compared per functional group possessed by the polymer gel and the comparative-use catalysts. With respect to the comparative-use catalysts, a homogeneous catalyst consisting of acetic acid and sodium acetate and a heterogeneous catalyst consisting of "ion exchange resin C-467" that is a commercial aminophosphate ion exchange resin were used. The concentration of acrolein was set in the range of 17% to 28%, and the reaction temperature was set at 80° C.

The results showed that in the case of the homogeneous catalyst consisting of acetic acid and sodium acetate, the reaction rate was 1.0 (mol/hr/catalyst-mol), that in the case of the heterogeneous catalyst consisting of the above-mentioned ion exchange resin, the reaction rate was in the range of 0.1 to 0.3 (mol/hr/catalyst-mol), and that in the case of the polymer gel formed in Embodiment 1, the reaction rate was in the range of 1.8 to 2.8 (mol/hr/catalyst-mol). It is found from the above results that the application of the polymer gel in accordance with the present invention makes it possible to provide a higher reaction rate than the heterogeneous catalyst, and the reaction rate is equivalent to or faster than that of the homogeneous catalyst.

Embodiment 37

The grainy resin (5) obtained in Embodiment 5 and the commercial strong basic ion exchange resin, "Amberlite IRA-400" (manufactured by Rohm & Haas Co.), were used as samples, and the heat resistances of the respective samples were compared through measurements on the thermal decomposition temperature and degradation tests under heat. The measurements on the thermal decomposition temperature and the degradation tests under heat were carried out in accordance with methods as described below.

<Thermal Decomposition Temperatures>

Each sample was heated at a rate of 5° C./min in a nitrogen gas flow by using a thermal-analysis measuring device, and based upon the thermogravimetric analysis—differential thermal analysis (TG-DTA) curve, the heat-absorption peak temperature resulting from the decomposition of the resin was defined as the thermal decomposition temperature.

<Degradation Test Under Heat>

Each sample was subjected to a heating process at 120° C. for 165 hours in ion exchange water in an atmosphere of air, and then measured in the rate of reduction of the N/C ratio by means of element analysis.

The results showed that the thermal decomposition temperature of the grainy resin (5) obtained in Embodiment 5 was 400° C., and the rate of reduction of the N/C ratio of the grainy resin (5) due to the application of heat was less than 1%. On the other hand, the thermal decomposition temperature of the strong basic ion exchange resin "Amberlite IRA-400" used for comparison was 290° C., and the rate of reduction of the N/C ratio due to the application of heat was 65%.

It is found from the results described above that the grainy resin (5) obtained in Embodiment 5 has a higher thermal decomposition temperature than the commercial strong basic ion exchange resin, exhibits higher heat resistance, is less susceptible to degradation under heat, and hardly releases nitrogen atoms.

Moreover, the grainy resin (5) obtained in Embodiment 5 was immersed in ion exchange water in a nitrogen sealed state, and allowed to stand at 120° C. for 500 hours; thus, the grainy resin (TD-11) was subjected to a heating treatment.

Next, a hydroxypropylation reaction of acrylic acid was carried out by using the same reactions and operations as those of Embodiment 29 except that the grainy resin that had been subjected to this heating treatment was used as the basic catalyst in Embodiment 29.

The results showed that the conversion of acrylic acid was 73%, that the selectivity of a propylene oxide 1-mole adduct (reaction product) in which one mole of propylene oxide was added to acrylic acid was 88%, and that the selectivity of a propylene oxide 2-mole adduct (reaction product from side reactions) in which two moles of propylene oxide was added to acrylic acid was 10%. Here, the conversion of the above-mentioned acrylic acid (reaction substrate) and the selectivities of the propyleneoxide 1-mole adduct and propyleneoxide 2-mole adduct are defined in the same manner as described earlier.

It is found from the results as described above that the grainy resin (5) obtained in Embodiment 5 is not susceptible to degradation in functions as a catalyst even when it undergoes a heating treatment.

Industrial Applicability

The polymer gel of the present invention has an intermediate mode as a substance between solid and liquid since it contains a solvent inside thereof; therefore, it exhibits superior operability in separation, elimination, etc. from the reaction system. Moreover, the polymer gel readily allows a solvent and a reaction substrate to be introduced therein, and has a higher degree of freedom in active sites as compared with the heterogeneous catalyst. Therefore, the application of the polymer gel as an activating catalyst makes it possible to activate the active-hydrogen-containing compound at the active sites inside the supporting structure and/or on the surface of the polymer gel, and consequently to activate the active-hydrogen-containing compound more efficiently.

In particular, the application of a polymer gel having a basic functional group makes it possible to carry out a reaction using a basic reaction system with high conversion at high reaction rates. There are a large number of important reactions using a basic reaction system in which the reaction takes place while using a basic resin having a basic functional group as a catalyst; therefore, the above-mentioned polymer gel is particularly useful for such reactions using a basic reaction system.

Moreover, the above-mentioned polymer gel is superior in the catalyst activity, and is allowed to react under milder reaction conditions as compared with the application of, for example, a solid catalyst; therefore, it is possible to reduce degradation at the time of reaction, to prevent the subsequent change in selectivity due to degradation, and also to reduce costs of catalyst.

Furthermore, in the case when the above-mentioned polymer gel is provided as a swelled matter of a high polymer compound having a cyclic amine structure in its main chain, since the high polymer compound is superior in heat resistance, the polymer gel consisting of the high polymer compound is also superior in heat resistance. For this reason, the polymer gel is less susceptible to separation of the basic functional group containing nitrogen atoms and degradation in activity resulting from elution of nitrogen atoms since it is hardly susceptible to degradation due to heat application; therefore, it can be stably used repeatedly for a long time.

What is claimed is:

1. An method for addition of a heterocyclic compound or an aldehyde to an active-hydrogen-containing compound, comprising the steps of activating an active-hydrogen-containing compound with a polymer gel having a swell ratio of not less than 2 and comprising a cyclic amine structure or a cyclic quaternary ammonium salt structure in the main chain of the polymer in the presence of a heterocyclic compound or an aldehyde under conditions conducive to the addition of the heterocyclic compound or the aldehyde to the active-hydrogen-containing compound.

2. The addition method of claim 1, wherein:

the active-hydrogen-containing compound is a compound selected from the group consisting of phenols, amides, alcohols, and carboxylic acids; and the heterocyclic compound is an oxirane compound.

3. The addition method of claim 1, wherein the polymer gel has a three-dimensional network structure holding solvent inside thereof and also has active sites for activating the active-hydrogen-containing compound inside the three-dimensional network structure and/or on the surface thereof.

4. The addition method of claim 1, wherein the cyclic amine structure or the cyclic quaternary ammonium salt structure in the polymer gel is derived from at least one selected from the group consisting of N,N,N-triallylamines, N,N-diallylamines, and diallyldimethylammonium chlorides.

5. The addition method of claim 1, wherein the polymer gel has a thermal decomposition temperature, that is, a heat-absorption peak temperature on a TG-DTA curve obtained when the polymer gel is heated at a rate of 5° C./min in a nitrogen gas flow, of not less than 300° C.

6. The addition method of claim 1, wherein:
the active-hydrogen-containing compound is (meth)acrylic acid and the heterocyclic compound is an oxirane compound, and
the (meth)acrylic acid is activated with the polymer gel under conditions conducive to the addition of the oxirane compound to the (meth)acrylic acid, so as to form a hydroxyalkyl(meth)acrylate.

7. The method of claim 1, wherein the active-hydrogen-containing compound is a carboxylic acid.

8. The method of claim 1, wherein the active-hydrogen-containing compound is an unsaturated carboxylic acid.

9. The method of claim 1, wherein the active-hydrogen-containing compound is acrylic acid.

10. The method of claim 1, wherein the active-hydrogen-containing compound is a phenol or a derivative thereof.

11. The method of claim 1, wherein the heterocyclic compound is an oxirane.

12. The method of claim 1, wherein the heterocyclic compound is ethylene oxide.

13. The method of claim 1, wherein the polymer gel is a copolymer of N,N-diallylamine hydrochloride and N,N,N-triallylamine hydrochloride.

14. The method of claim 1, wherein
active-hydrogen-containing compound is acrylic acid;
the heterocyclic compound is ethylene oxide; and
the polymer gel is a copolymer of N,N-diallylamine hydrochloride and N,N,N-triallylamine hydrochloride.

15. The addition method of claim 1, wherein the polymer gel has a ratio of swell in a range of 2.5 to 10.

16. The addition method of claim 1, wherein the polymer gel has a ratio of swell in a range of 3 to 8.

* * * * *